United States Patent
Frangakis et al.

(10) Patent No.: US 11,026,882 B2
(45) Date of Patent: Jun. 8, 2021

(54) METHODS AND COMPOSITIONS FOR TREATING MIGRAINE AND CONDITIONS ASSOCIATED WITH PAIN

(71) Applicant: Achelios Therapeutics, Inc., Chapel Hill, NC (US)

(72) Inventors: Crist J. Frangakis, Chapel Hill, NC (US); William Bauer, Port Clinton, OH (US); Wolfgang Liedtke, Durham, NC (US)

(73) Assignee: Achelios Therapeutics, Inc., Chapel Hill, NC (US)

(*) Notice: Subject to any disclaimer, the term of this patent is extended or adjusted under 35 U.S.C. 154(b) by 0 days.

(21) Appl. No.: 16/234,069

(22) Filed: Dec. 27, 2018

(65) Prior Publication Data

US 2019/0216720 A1  Jul. 18, 2019

Related U.S. Application Data

(62) Division of application No. 15/532,425, filed as application No. PCT/US2015/063220 on Dec. 1, 2015, now abandoned.

(60) Provisional application No. 62/085,943, filed on Dec. 1, 2014.

(51) Int. Cl.
| | | |
|---|---|---|
| A61K 31/14 | (2006.01) |
| A61K 9/00 | (2006.01) |
| A61K 9/06 | (2006.01) |
| A61K 47/32 | (2006.01) |
| A61K 31/196 | (2006.01) |
| A61K 31/405 | (2006.01) |
| A61K 31/407 | (2006.01) |
| A61K 31/415 | (2006.01) |
| A61K 31/5415 | (2006.01) |
| A61K 31/616 | (2006.01) |
| A61K 31/635 | (2006.01) |
| A61P 25/06 | (2006.01) |
| A61K 31/192 | (2006.01) |
| A61K 45/06 | (2006.01) |

(52) U.S. Cl.
CPC .............. *A61K 9/0014* (2013.01); *A61K 9/06* (2013.01); *A61K 31/14* (2013.01); *A61K 31/192* (2013.01); *A61K 31/196* (2013.01); *A61K 31/405* (2013.01); *A61K 31/407* (2013.01); *A61K 31/415* (2013.01); *A61K 31/5415* (2013.01); *A61K 31/616* (2013.01); *A61K 31/635* (2013.01); *A61K 45/06* (2013.01); *A61K 47/32* (2013.01); *A61P 25/06* (2018.01)

(58) Field of Classification Search
CPC ................................ A61K 31/19; A61K 31/14
See application file for complete search history.

(56) References Cited

U.S. PATENT DOCUMENTS

| | | | |
|---|---|---|---|
| 3,759,980 A * | 9/1973 | Rosen ................... | A61K 31/60 560/143 |
| 4,532,244 A | 7/1985 | Innes | |
| 4,877,805 A | 10/1989 | Kligman | |
| 4,975,282 A | 12/1990 | Cullis et al. | |
| 4,980,378 A | 12/1990 | Wong et al. | |
| 4,994,213 A | 2/1991 | Aitcheson et al. | |
| 5,000,958 A | 3/1991 | Fountain et al. | |
| 5,023,087 A | 6/1991 | Yau-Young | |
| 5,032,582 A | 7/1991 | Abra | |
| 5,049,388 A | 9/1991 | Knight et al. | |
| 5,082,866 A | 1/1992 | Wong et al. | |
| 5,169,637 A | 12/1992 | Lenk et al. | |
| 5,194,266 A | 3/1993 | Abra et al. | |
| 5,356,633 A | 10/1994 | Woodle et al. | |
| 5,409,704 A | 4/1995 | Bally et al. | |
| 5,552,155 A | 9/1996 | Bailey et al. | |
| 5,667,799 A | 9/1997 | Caldwell et al. | |
| 5,688,525 A | 11/1997 | Adler-Moore et al. | |
| 5,856,355 A | 1/1999 | Richter et al. | |
| 5,874,104 A | 2/1999 | Adler-Moore et al. | |
| 5,914,129 A * | 6/1999 | Mauskop ............... | A61K 45/06 424/464 |
| 6,083,996 A | 7/2000 | Buyuktimkin et al. | |
| 6,090,368 A | 7/2000 | Zia et al. | |
| 6,118,020 A | 9/2000 | Buyuktimkin et al. | |
| 6,139,861 A | 10/2000 | Friedman | |
| 6,221,377 B1 | 4/2001 | Meyer | |
| 6,387,407 B1 | 5/2002 | Drizen et al. | |
| 6,896,898 B1 | 5/2005 | Xiong et al. | |

(Continued)

FOREIGN PATENT DOCUMENTS

| | | |
|---|---|---|
| EP | 0586106 A1 | 3/1994 |
| JP | 2000500449 A | 1/2000 |

(Continued)

OTHER PUBLICATIONS

Badel et al. et al. CAS: 70088408, 2009.*

(Continued)

*Primary Examiner* — Rei Tsang Shiao
(74) *Attorney, Agent, or Firm* — Clark & Elbing LLP

(57) ABSTRACT

The present invention relates to pharmaceutical compositions of a non-steroidal anti-inflammatory drug (NSAIDs) such as, aspirin, diclofenac, ibuprofen, ketoprofen, or naproxen, or any pharmaceutically acceptable salts, solvates, or prodrugs thereof, and the medical use of these compositions. The compositions, which can be formulated for topical administration, can provide extended release of the NSAIDs. The compositions of the invention are useful, for example, in the prophylactic treatment or treatment and/or reduction of pain, in the prophylactic treatment or treatment of headaches such as migraine headaches and symptoms of migraine headaches, and in the treatment of temporomandibular disorders (TMD).

14 Claims, 18 Drawing Sheets

(56) References Cited

U.S. PATENT DOCUMENTS

| | | |
|---|---|---|
| 8,822,537 B2 * | 9/2014 | Buyuktimkin ......... A61K 47/32 514/557 |
| 8,883,143 B2 | 11/2014 | Binder |
| 9,629,920 B2 | 4/2017 | Leighton et al. |
| 2001/0055607 A1 | 12/2001 | Levin |
| 2002/0099060 A1 | 7/2002 | Imanzahrai |
| 2002/0143047 A1 | 10/2002 | Galer et al. |
| 2003/0013753 A1 | 1/2003 | Aung-Din |
| 2003/0040537 A1 | 2/2003 | Plachetka et al. |
| 2003/0119892 A1 | 6/2003 | Caldwell et al. |
| 2004/0138239 A1 | 7/2004 | Frome |
| 2004/0185123 A1 | 9/2004 | Mazzio et al. |
| 2005/0019354 A1 | 1/2005 | Perricone |
| 2005/0090557 A1 | 4/2005 | Muhammad et al. |
| 2005/0095277 A1 | 5/2005 | Ozturk et al. |
| 2006/0178354 A1 | 8/2006 | Lucas |
| 2007/0093420 A1 | 4/2007 | Yeomans et al. |
| 2007/0112052 A9 | 5/2007 | Caldwell et al. |
| 2008/0279895 A1 | 11/2008 | Blumenfeld |
| 2008/0317684 A1 | 12/2008 | Spann-Wade et al. |
| 2009/0123528 A1 | 5/2009 | Fossel |
| 2009/0214466 A1 | 8/2009 | Levin |
| 2009/0258884 A1 | 10/2009 | Hagmann et al. |
| 2009/0281080 A1 | 11/2009 | Bell et al. |
| 2009/0312435 A1 | 12/2009 | Gant et al. |
| 2013/0053393 A1 | 2/2013 | Frangakis et al. |
| 2013/0059019 A1 | 3/2013 | Leighton et al. |
| 2013/0109674 A1 * | 5/2013 | Leighton ............... A61K 9/0014 514/217 |
| 2013/0209585 A1 | 8/2013 | Kim |
| 2014/0088195 A1 * | 3/2014 | Buyuktimkin ......... A61K 47/32 514/570 |
| 2014/0178459 A1 | 6/2014 | Kisak et al. |
| 2018/0369174 A1 | 12/2018 | Frangakis et al. |
| 2019/0105290 A1 | 4/2019 | Leighton et al. |

FOREIGN PATENT DOCUMENTS

| | | |
|---|---|---|
| JP | 2002511057 A | 4/2002 |
| JP | 2007532696 A | 11/2007 |
| JP | 2009506076 A | 2/2009 |
| JP | 2012-092123 A | 5/2012 |
| JP | 2013-515002 A | 5/2013 |
| WO | WO-96/40061 A1 | 12/1996 |
| WO | WO-97/17978 A1 | 5/1997 |
| WO | WO-98/34592 A1 | 8/1998 |
| WO | WO-98/42275 A1 | 10/1998 |
| WO | WO-03/032983 A1 | 4/2003 |
| WO | WO-2004/075832 A2 | 9/2004 |
| WO | WO-2005/074913 A2 | 8/2005 |
| WO | WO-2005/102282 A1 | 11/2005 |
| WO | WO-2007/025286 A2 | 3/2007 |
| WO | WO-2008/054788 A2 | 5/2008 |
| WO | WO-2011/017122 A1 | 2/2011 |
| WO | WO-2011/075654 A1 | 6/2011 |
| WO | WO-2011/075655 A1 | 6/2011 |
| WO | WO-2011/075688 A1 | 6/2011 |
| WO | WO-2011/075691 A1 | 6/2011 |
| WO | WO-2013/125518 A1 | 8/2013 |
| WO | WO-2014/052313 A1 | 4/2014 |

OTHER PUBLICATIONS

Bouloux, J Oral Maxillofac Surg, 2011,69(7): 1885-91 (abstract).*
U.S. Appl. No. 13/517,008, Leighton et al.
U.S. Appl. No. 13/517,010, Frangakis et al.
U.S. Appl. No. 13/517,024, filed Apr. 25, 2017, Leighton et al.
"Cervicogenic headache," American Migraine Foundation, available <https://americanmigrainefoundation.org/living-with-migraines/types-of-headachemigraine/cervicogenic-headache/>, accessed Oct. 4, 2016 (7 pages).
"Igaku Dai Jiten (Medical Dictionary)", Japan, (published in 2003), p. 577, 693 (3 pages).
"Wakariyasui Kaiboseiri (Comprehensible anatomical physiology)", Japan, (published in 2001), 2nd Ed., pp. 63-68.
Brown, "Prescribing flexibility through prescription compounding," Tech Reg Anesth and Pain Manag. 12(2):119-21 (2008).
Medline Database [online], US National Library of Medicine (NLM), Bethesda, MD: Göbel, H. et al.: "[Effectiveness of Oleum menthae piperitae and paracetamol in therapy of headache of the tension type]," Database accession No. NLM8805113 (1996) (2 pages).
Database Medline Accession No. NLM8805113 (2 pages).
Differential Diagnosis of Headache. Merck Manual. Berkow, R. and Fletcher, A.J., 15:1352-4(1987).
Dogan et al., "Effects of high-frequency bio-oxidative ozone therapy in temporomandibular disorder-related pain," Med Princ Pract. 23(6):507-10 (2014).
English Translation of Notice of Reasons for Rejection for Japanese Patent Application No. 2012-544917, dated Dec. 16, 2014, (3 pages).
European Patent Office Communication for European Patent Application No. 10 838 320.9, dated Nov. 5, 2013 (10 pages).
Examination Report for Australian Application No. 2016256779, dated Oct. 10, 2017 (6 pages).
Extended European Search Report for European Application No. 15864857.6, dated Jul. 11, 2018 (9 pages).
Extended European Search Report for European Patent Application No. 10838320.9, dated Apr. 8, 2014 (15 pages).
Final Rejection for Japanese Patent Application No. 2012-544917, dated Oct. 20, 2015 (4 pages).
Fortier et al., "Review of biomechanical studies of arteries and their effect on stent performance," IJC Heart & Vessels. 4:12-8 (2014).
Friedman et al., "Intraoral topical nonsteroidal antiinflammatory drug application for headache prevention," Heart Dis. 4(4):212-5 (2002).
Friedman, "Local inflammation as a mediator of migraine and tension-type headache," Headache. 44(8):767-771 (2004).
Gobel et al., "[Effectiveness of Oleum menthae piperitae and paracetamol in therapy of headache of the tension type]," Nervenarzt. 67(8):672-81 (1996). English Abstract Only.
Goncalves et al., "How to investigate and treat: migraine in patients with temporomandibular disorders," Curr Pain Headache Rep. 16(4):359-64 (2012) (Abstract only).
Heir et al., "Use of topical medication in orofacial neuropathic pain: a retrospective study," Oral Surg, Oral Med, Oral Pathol, Oral Radiol Endod. 105(4):466-9 (2008).
Hersh et al., "Topical capsaicin-pharmacology and potential role in the treatment of temporomandibular pain," J Clin Dent. 5(2):54-9 (1994).
Highlights of Prescribing Information for FLECTOR® PATCH (diclofenac epolamine) 1.3%, King Pharmaceuticals Inc., revised Aug. 2011 (23 pages).
International Search Report and Written Opinion for International Application No. PCT/US2010/061130, dated Mar. 7, 2011 (9 pages).
International Search Report and Written Opinion for International application No. PCT/US2015/063220, dated Feb. 9, 2016 (18 pages).
International Search Report and Written Opinion for International Application No. PCT/US2016/067276, dated Mar. 9, 2017 (17 pages).
Journal of Clinical and Experimental Medicine (Igaku No Ayumi), vol. 215, No. 14 (2005), pp. 1027-1031.
Lewis et al., Anatomy of the Human Body. Lea & Febiger, 432-3 and 892-5 (1918).
Liedtke et al., "Topically applied ketoprofen gel (ELS-M11) in the treatment of severe migraine pain," Neurology. 85(4):e47 (2015).
Martelletti et al., "Role of NSAIDs in acute treatment of headache," Drug Dev Res. 68(6):276-81 (2007).
Moore et al., "Quantitative systematic review of topically applied non-steroidal anti-inflammatory drugs," BMJ. 316(7128):333-8 (1998).
Nakamura et al., "Classification and criteria of tension-type headache," Journal of Clinical and Experimental Medicine (Igaku No Ayumi), 215(14):1039-42 (2005).
Notice of Reasons for Rejection for Japanese Patent Application No. 2012-544917, dated Dec. 6, 2016 (23 pages).

(56) References Cited

OTHER PUBLICATIONS

Office Action for Canadian Application No. 2,784,824, dated Sep. 22, 2016 (6 pages).
Sjaastad et al., "Cervicogenic headache. The differentiation from common migraine. An overview," Funct Neurol. 6(2):93-100 (1991). Abstract only.
Van Haaren et al., "Localization of the permeability barrier to solutes in isolated arteries by confocal microscopy," Am J Physiol Heart Circ Physiol. 285(6):H2848-56 (2003).
Rajanandh et al., "Assessment of antioxidant supplementation on the neuropathic pain score and quality of life in diabetic neuropathy patients—a randomized controlled study," Pharmacol Rep. 66(1):44-8 (2014).
Office Action for Chinese Patent Application No. 201580075227.5, dated Jan. 22, 2020 (16 pages).
Notice of Reasons for Rejection for Japanese Patent Application No. 2017-547930, dated Sep. 24, 2019 (12 pages).
Di Rienzo Businco et al., "Topical Versus Systemic Diclofenac in the Treatment of Temporo-Mandibular Joint Dysfunction Symptoms," Acta Otorhinolaryngol Ital. 24(5): 279-83 (2004).
Communication Pursuant to Article 94(3) for European Patent Application No. 15864857.6, dated Jan. 29, 2020 (5 pages).
Haroutiunian et al., "Topical NSAID Therapy for Musculoskeletal Pain," Pain Med. 11(4): 535-49 (2010).
Office Action for Japanese Patent Application No. 2020-001791, dated Dec. 16, 2020 (7 pages).
Office Action for Chinese Patent Application No. 201580075227.5, dated Nov. 26, 2020 (4 pages).
Goncalves et al., "How to investigate and treat: migraine in patients with temporomandibular disorders" Curr Pain Headache Rep. 16(4):359-64 (2012).
Thomas et al., "Migraine treatment by oral magnesium intake and correction of the irritation of buccofacial and cervical muscles as a side effect of mandibular imbalance," Magnes Res. 7(2):123-7 (1994).
Van der Meer et al., "Effects of physical therapy for temporomandibular disorders on headache pain intensity: A systematic review," Musculoskelet Sci Pract., 50(102277): 1-10 (2020) (10 pages).
Duvall et al., "Clinical Reasoning: an underrecognized etiology of new daily persistent headache," Neurology., 94(1): e114-e120 (2020) (8 pages).

* cited by examiner n=10 mice per group

__US 11,026,882 B2__

METHODS AND COMPOSITIONS FOR TREATING MIGRAINE AND CONDITIONS ASSOCIATED WITH PAIN

FIELD OF INVENTION

The invention relates to methods and compositions for treating conditions associated with pain and particularly for treating headaches, including migraine headaches.

BACKGROUND OF THE INVENTION

Pain is a major symptom in many medical conditions and can significantly interfere with a subject's quality of life and general functioning. Three categories of pain are generally recognized: nociceptive pain, which is caused by stimulation of peripheral nerve fibers; inflammatory pain, which is associated with tissue damage and the infiltration of immune cells; and pathological pain, which is a disease state caused by damage to the nervous system or by its abnormal function (e.g., dysfunctional pain in condition such as fibromyalgia, irritable bowel syndrome, and tension type headache).

Migraine is a common disorder characterized by intermittent attacks of moderate-to-severe head pain associated with nausea, photophobia, and phonophobia. An aura (i.e., vision changes) precedes other symptoms in approximately 10 to 20% of subjects affected with a migraine. It is estimated that over half of subjects experiencing a migraine remain undiagnosed. Migraine is a common and disabling brain disorder with a strong inherited component. Because subjects experiencing a migraine have severe and disabling attacks, usually of headache with other symptoms of sensory disturbance (e.g., light and sound sensitivity), medical treatment is often required.

Treatments currently consist of nonspecific therapy with medications that relieve pain, including non-steroidal anti-inflammatory drugs (NSAIDs) and specific abortive medications such as triptans or ergot derivatives. In the past decade, the serotonin (5HT)1 agonists have become a mainstay of therapy. A major limitation of serotonin agonists, including sumatriptan, is lack of early efficacy followed by migraine recurrence in 25-78% of those treated. The reason for recurrence is not known. Thus, despite the development and availability of these migraine-specific medications, only 19% of subjected affected with a migraine use triptans for acute therapy and triptan satisfaction is generally modest, at best.

NSAIDs that are being used increasingly to treat acute migraine, include, for example, Trexima™ (a combination drug consisting of a single tablet containing sumatriptan succinate and naproxen sodium), Advil® Migraine (ibuprofen), Cambia™ (diclofenac potassium), Aleve® (naproxen), and Orudis®/Oruvail® (ketoprofen). All of these agents have a common property in that they inhibit prostaglandin synthesis thereby reducing the consequences of the inflammatory reaction, whether it be from different origin or mechanism. The headache phase of migraine may develop as a result of an abnormal interaction and perhaps an abnormal release of vaso-active neurotransmitters from terminals of the trigeminal nerve with large intracranial and extra cranial blood vessels. These blood vessels, which dilate during the headache phase of migraine, are thought to receive axonal projections from all three divisions of the trigeminal nerve. By modulating neurotransmitter release, NSAIDs potentiate and inhibit sympathetic neural transmission. NSAIDs also promote the contraction and relaxation of vascular smooth muscles, enhance vascular permeability, and mediate the actions of other vasoactive substances.

Other NSAIDs can be classified based on their chemical structure or mechanism of action. Common NSAID classification groups include: salicylates, propionic acid derivatives, acetic acid derivatives, enolic acid derivatives, fenamic acid derivatives, selective COX-2 inhibitors, and sulphonamides. NSAIDs within a group tend to have similar characteristics and tolerability. There is little difference in clinical efficacy among the NSAIDs when used at equivalent doses. Rather, differences among the compounds relate to dosing regimens, route of administration, and tolerability profile.

Although subjects often prefer the convenience of oral therapy of the above-mentioned NSAIDs, these medications can have numerous side effects, for example, nausea, vomiting, and gastrointestinal and renal effects that can sometimes limit the effectiveness of this route of administration. Accordingly, there exists a need in the medical field to develop safe and effective formulations of NSAIDs that minimize systemic side effects and gastrointestinal irritation to treat conditions associated with pain, migraine, and temporomandibular disorders.

SUMMARY OF THE INVENTION

In one aspect, the present invention features a method of treating or reducing the likelihood of a migraine in a subject in need thereof, the method including topically administering to the subject a sustained release composition including from about 0.5% (w/w) to about 5% (w/w) of a therapeutic agent and a dermatologically acceptable excipient, wherein the composition is in an amount effective to treat or reduce the likelihood of a migraine in the subject and wherein administration of the composition to the subject results in a peak plasma concentration of the therapeutic agent at three hours that is at most about 450 ng/mL.

In a second aspect, the present invention features a method for prophylactic reduction of a migraine or symptom of a migraine in a subject in need thereof, the method including topically administering to the subject a sustained release composition including form about 0.5% (w/w) to about 5% (w/w) of a therapeutic agent and a dermatologically acceptable excipient, wherein the composition is in an amount effective to prophylactically reducing a migraine or a symptom of a migraine and wherein administration of the composition to the subject results in peak plasma concentration of the therapeutic agent at three hours that is at most about 450 ng/mL.

In one embodiment, the composition is administered at a time prior to when the subject expects to experience a migraine-triggering stimulus, wherein the time prior to is at least 3 hours or at least one day. In another embodiment, the migraine-triggering stimulus is selected from the group consisting of: stress, change in routine, sleep, environmental stimuli, hormonal spikes, glare, food, lack of food, additives, alcohol, mild dehydration, drugs, exercise, oral contraceptives, teeth grinding, or physical conditions. In yet another embodiment, the subject has a history of a migraine or is predisposed to having a migraine. In another embodiment, the subject has been or is involved in pre-monitoring symptoms of a migraine.

In certain embodiments of the above aspects, the method further ameliorates a symptom of migraine, wherein the symptom of a migraine is selected from the group consisting of: severe headache, nausea, muscle tenderness, abdominal pain, visual aura, sensory hyper excitability, blurred vision, nasal congestion, diarrhea, polyuria, pallor, sweating, localized edema of the scalp or face, scalp tenderness, prominence of a vein or artery in the temple, stiffness or tenderness of the neck, impairment of concentration or mood, vertigo, lightheadedness, fatigue, depression, and euphoria. In certain other embodiments, the composition further reduces the frequency or duration of the migraine. In a third aspect, the present invention features a method of treating a temporomandibular disorder (TMD) in a subject in need thereof, the method including topically administering to the subject a sustained release composition including from about 0.5% (w/w) to about 5% (w/w) of a therapeutic agent and a dermatologically acceptable excipient, wherein the composition is in an amount effective to treat the temporomandibular disorder (TMD) in the subject and wherein administration of the composition to the subject results in a peak plasma concentration of the therapeutic agent at three hours that is at most about 450 ng/mL.

In certain embodiments, the method further including monitoring whether the subject experiences amelioration of a symptom of TMD, wherein the symptom of TMD is selected from the group consisting of: a toothache, headache, neck ache, dizziness, earache, upper shoulder pain, tenderness in the face, pain in the temporomandibular joint or its surrounding tissues, functional limitations of the mandible, clicking in the temporomandibular joint during motion, and swelling of the face.

In one embodiment of the above aspects, the peak plasma concentration of the therapeutic agent when administered topically is lower than the peak plasma concentration of the therapeutic agent when administered orally. In a second embodiment, administration of the composition to the subject provides for gradual release of the therapeutic agent over 2-24 hours. In a third embodiment, administration of the composition results in a plasma concentration of the therapeutic agent that is maintained between about 50 ng/mL and about 150 ng/mL for up to 24 hours. In a fourth embodiment, the half-life of the therapeutic agent is between about 7 to about 13 hours (e.g., about 7.5, 8, 8.5, 9, 9.5, 10, 10.5, 11, 11.5, 12, 12.5, or 13). In a fifth embodiment, the therapeutic agent is a non-steroidal anti-inflammatory drug (NSAID) or a pharmaceutically acceptable salt thereof.

In particular embodiments, the NSAID or a pharmaceutically acceptable salt thereof is selected from the group consisting of: aspirin, choline and magnesium salicylates and salts thereof, celecoxib, diclofenac and salts thereof, diflunisal, etodolac, fenoprofen and salts thereof, flurbiprofen, ibuprofen, indomethacin, ketoprofen, meclofenamate and salts, thereof, mefenamic acid, meloxicam, nabumetone, naproxen and salts thereof, oxaprozin, piroxicam, rofecoxib, salsalate, sulindac, tolmetin and salts thereof, and valdecoxib. In preferred embodiments, the NSAID or a pharmaceutically acceptable salt thereof is ketoprofen. In other preferred embodiments, the composition includes from about 20 mg to about 200 mg of ketoprofen in unit dosage form (e.g., about 21 mg, 22 mg, 22.5 mg, 23 mg, 24 mg, 30 mg, 50 mg, 65 mg, 75 mg, 100 mg, 125 mg, etc). In other embodiments, the composition includes a total maximum dosage of about 135 mg of ketoprofen. In certain embodiments, the composition is formulated as a gel, cream, lotion, ointment, foam, powder, solution, spray, emulsion, or suspension for topical administration. In preferred embodiments, the composition is formulated as a gel for topical administration.

In certain other embodiments, the composition is administered one or more times a day. In other embodiments, the composition is administered for one day or at least two to twenty days. In yet other embodiments, the composition is administered for more than twenty days. In particular embodiments, the composition is administered with a second agent, wherein the second agent is selected from the group consisting of: a corticosteroid, acetaminophen, an opioid, a muscle relaxant, an anti-anxiety drug, an antidepressant, an anti-convulsant drug, an antipsychotic, an antiepileptic drug, and a selective serotonin reuptake inhibitor (SSRI).

Definitions

As used herein, the term "administration" or "administering" refers to a method of giving a dosage of a composition to a subject. The preferred method of administration may depend on a variety of factors, e.g., the components of the composition and the nature and severity of the disease, disorder, or condition. The phrase "administered together" means that two or more therapeutic agents (e.g., any of the NSAIDs described herein) are formulated together in a single composition or two or more therapeutic agents (e.g., any of the NSAIDs described herein) are administered in combination to the subject.

As used herein, the phrase "an amount effective" refers to an amount of at least one therapeutic agent that prevents a condition associated with pain, migraine, and temporomandibular disorders, diminishes the frequency or intensity of pain, migraine, and temporomandibular disorders, or relieves one or more symptoms caused by pain associated with migraine, migraine, and temporomandibular disorders. As such, the phrase "an effective amount" refers to an amount of at least one therapeutic agent that prevents, treats, or palliates a disease, a disorder, or a condition as described herein.

By "chronic pain" is meant pain that lasts longer than three to six months or pain that extends beyond the expected period of healing. Chronic pain may originate with an initial trauma/injury or infection, or may be an ongoing cause of pain, headaches, joint pain, backaches, sinus pain, muscle pain, nerve pain, and pain affecting specific parts of the body, such as shoulders, pelvis, and neck. Chronic pain may also be associated with chronic migraine that relates to having more than 15 migraine headaches a month. Chronic pain may also be associated with lower back pain, arthritis, headache, multiple sclerosis, fibromyalgia, shingles, nerve damage, or cancer.

The phrase "dermatologically acceptable excipient" means that the compositions or components thereof are suitable for use in contact with dermal tissue without undue toxicity, incompatibility, instability, allergic response, and the like. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltose, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The terms "extended release" or "sustained release" interchangeably refer to a drug formulation that provides for gradual release of a drug over an extended period of time, e.g., 2-24 hours or more (e.g., 2-4 hours, 2-8 hours, 2-10 hours, 2-15 hours, 2-20 hours, 4-8 hours, 4-10 hours, 4-20 hours, 8-10 hours, 8-15 hours, 10-15 hours, 15-20 hours, 20-25 hours), compared to an immediate release formulation of the same drug or therapeutic agent. Preferably, although not necessarily, results in substantially constant blood levels of a drug or therapeutic agent over an extended time period that are within therapeutic levels and fall within a peak plasma concentration range that is between, for example from about 50 ng/mL to about 150 ng/mL (e.g., about 50 ng/mL to about 75 ng/mL, about 50 ng/mL to about 100 ng/mL, about 50 ng/mL to about 125 ng/mL, about 80 ng/mL to about 100 ng/mL, about 90 ng/mL to about 100 ng/mL, about 105 ng/mL to about 115 ng/mL, about 105 ng/mL to about 120 ng/mL, about 110 ng/mL to about 120 ng/mL, about 120 ng/mL to about 130 ng/mL, about 130 ng/mL to about 145 ng/mL, about 145 ng/mL to about 150 ng/mL).

By "headache" is meant any type of headache, including, but not limited to, a migraine headache, a tension headache, or a cluster headache.

By "migraine" is meant a subset of headaches characterized by unusually severe, unilateral, throbbing head pain that often includes additional symptoms described herein. Migraine is meant to include, for example, migraine without aura (e.g., common migraine), migraine with aura (e.g., classical migraine), migraine with typical aura, migraine with prolonged aura, migraine without headache, hemiplegic migraine (e.g., familial hemiplegic migraine), basilar migraine (e.g., basilar artery migraine), carotidynia, abdominal migraine (e.g., periodic syndrome), hormonal migraine (e.g., pregnancy-induced migraine), exertion migraine, migraine with acute onset aura, ophthalmoplegic migraine, status migrainous, transformed migraine, retinal migraine, nocturnal migraine, childhood periodic syndromes that may be precursors to or associated with migraine, benign paroxysmal vertigo of childhood, alternating hemiplegia of childhood, and migrainous infarction. Symptoms of migraines include, e.g., severe headache, nausea, muscle tenderness, abdominal pain, visual aura, sensory hyperexcitability (e.g., photophobia, phonophobia, or osmophobia), tinnitus, vomiting, dizziness, pale or clammy skin, blurred vision, nasal congestion, diarrhea, polyuria, pallor, sweating, localized edema of the scalp or face, scalp tenderness, prominence of a vein or artery in the temple, stiffness or tenderness of the neck, impairment of concentration or mood, vertigo, lightheadedness, fatigue, depression, and euphoria.

The term "pharmaceutically acceptable salt," as used herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds of the invention or separately by reacting the free base group with a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

By "predisposition or is diagnosed" is meant a population of subjects (e.g. mammals, including humans and non-humans) that has been pre-selected as having a condition associated with pain, a mood disorder and/or an imbalance in psychological state, or a disorder of brain development. The conditions associated with pain include but are not limited to: musculo-skeletal pain (after trauma, infections), pain associated with traumatic injury, spinal cord injury, tumors, compression, inflammation, dental pain, episiotomy pain, deep and visceral pain (e.g., heart pain, bladder pain, or pelvic organ pain), muscle pain, eye pain, orofacial pain (e.g., odontalgia, trigeminal neuralgia, glossopharyngeal neuralgia), abdominal pain, gynecological pain (e.g., dysmenorrhea and labor pain), pain associated with nerve and root damage due to trauma, compression, inflammation, toxic chemicals, hereditary conditions, central nervous system pain, such as pain due to spinal cord or brain stem damage, cerebrovascular accidents, tumors, infections, demyelinating diseases including multiple sclerosis, low back pain, sciatica, and post-operative pain.

By "prevention" is meant that a prophylactic treatment is given to a subject who has or will have a disease, a disorder, a condition, or one or more symptoms associated with a disease, a disorder, or a condition.

By "reduction or reducing" of a disease, a disorder, or a condition is meant that the extent and/or undesirable clinical manifestations of the disease, disorder, or condition are lessened and/or the time course of the progression is slowed or lengthened, as compared to the extent or time course in the absence of treatment.

By "subject" is meant a mammal, including, but not limited to, a human or non-human mammal.

By "treatment" is meant an approach for obtaining beneficial or desired results, such as clinical results. Beneficial or desired results can include, but are not limited to, alleviation, amelioration, or prevention of a disease, a disorder, a condition, or one or more symptoms associated with a disease, a disorder, or a condition; diminishment of extent of disease, disorder, or condition; stabilization (i.e., not worsening) of a disease, disorder, or condition; delay or slowing the progress of a disease, disorder, or condition; and amelioration or palliation of a disease, disorder, or condition. "Treatment" can also mean prolonging survival as compared to expected survival if not receiving treatment.

By "therapeutic agent" is meant any agent that produces a healing, curative, stabilizing, or ameliorative effect.

The recitation herein of numerical ranges by endpoints is intended to include all numbers subsumed within that range (e.g. a recitation of 1 to 5 includes 1, 1.5, 2, 2.75, 3, 3.80, 4, and 5).

As used herein, "about" refers to an amount±10 of the recited value.

As used herein, "a" or "an" means "at least one" or "one or more" unless otherwise indicated. In addition, the singular forms "a", "an", and "the" include plural referents unless the context clearly dictates otherwise. Thus, for example, reference to a composition containing "a therapeutic agent" includes a mixture of two or more therapeutic agents.

Other features and advantages of the invention will be apparent from the following Detailed Description and from the claims.

BRIEF DESCRIPTION OF THE DRAWINGS

FIGS. 10A and 10B are graphs showing rubbing of the mouse whisker pad (measure of pain behavior) over time of formalin injection. FIG. 10C is a graph showing the effects of ELS-M10 on pain behavior as measured by rubbing of the whisker pad.

DETAILED DESCRIPTION

Figure 1A:
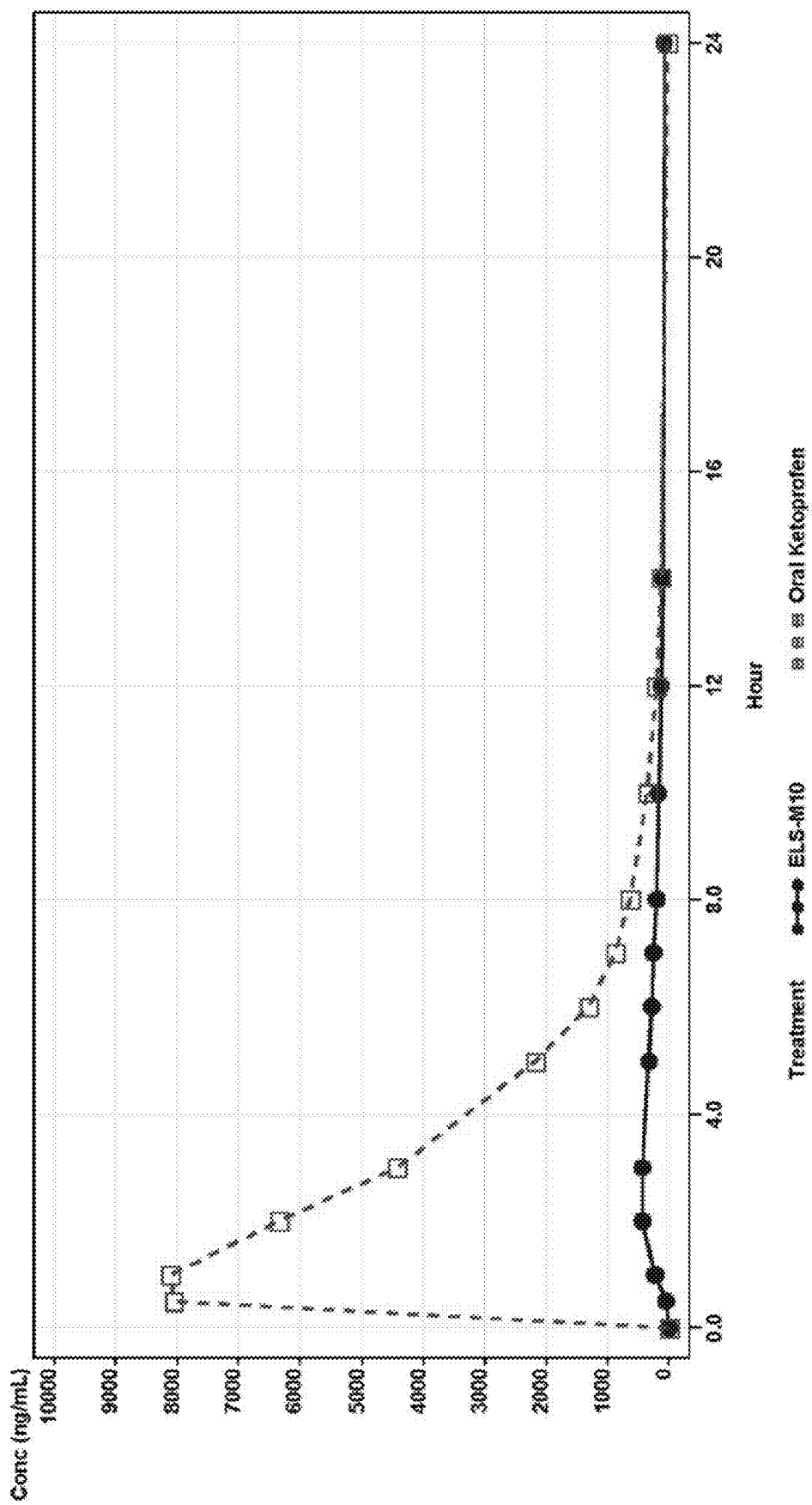
FIGS. 1A-1B are linear-linear (FIG. 1A) and log-linear (FIG. 1B) plots depicting the mean plasma ketoprofen concentration vs. time following administration of an oral ketoprofen formulation and the topical ketoprofen formulation, ELS-M10.
Figure 1B:
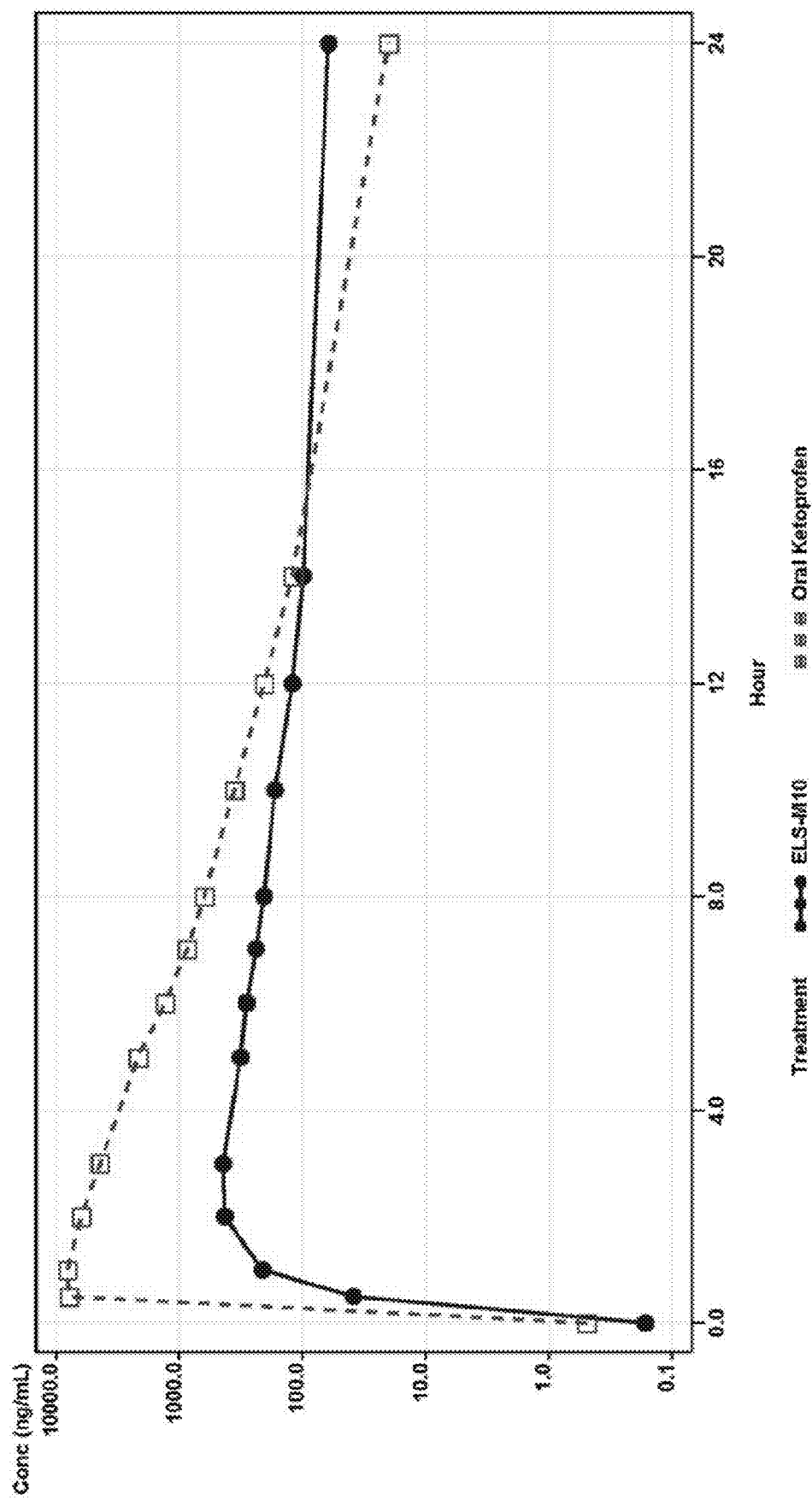
Figure 2A:
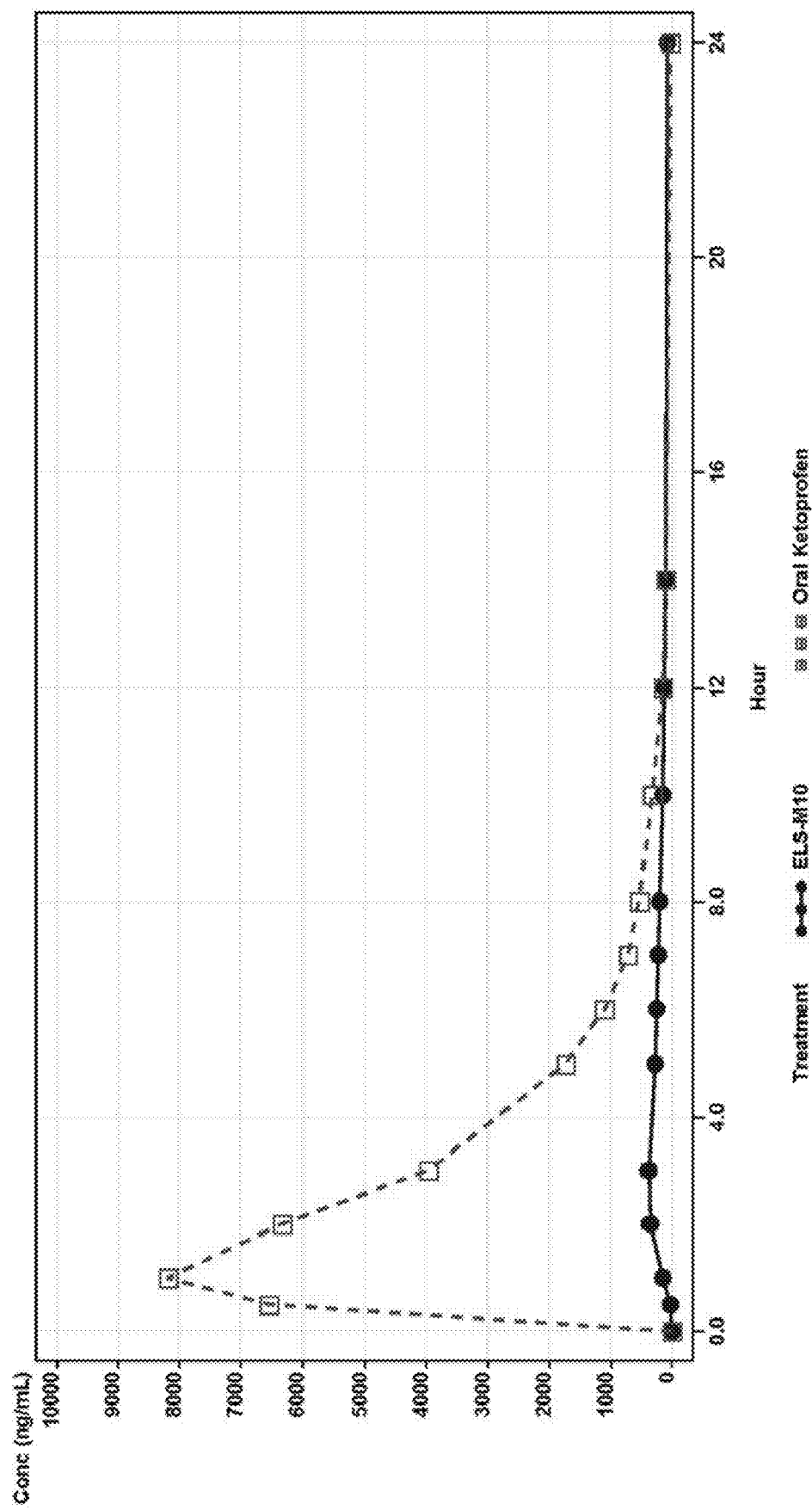
FIGS. 2A-2B are linear-linear (FIG. 2A) and log-linear (FIG. 2B) plots depicting the median plasma ketoprofen concentration vs. time following administration of an oral ketoprofen formulation and the topical ketoprofen formulation, ELS-M10.
Figure 2B:
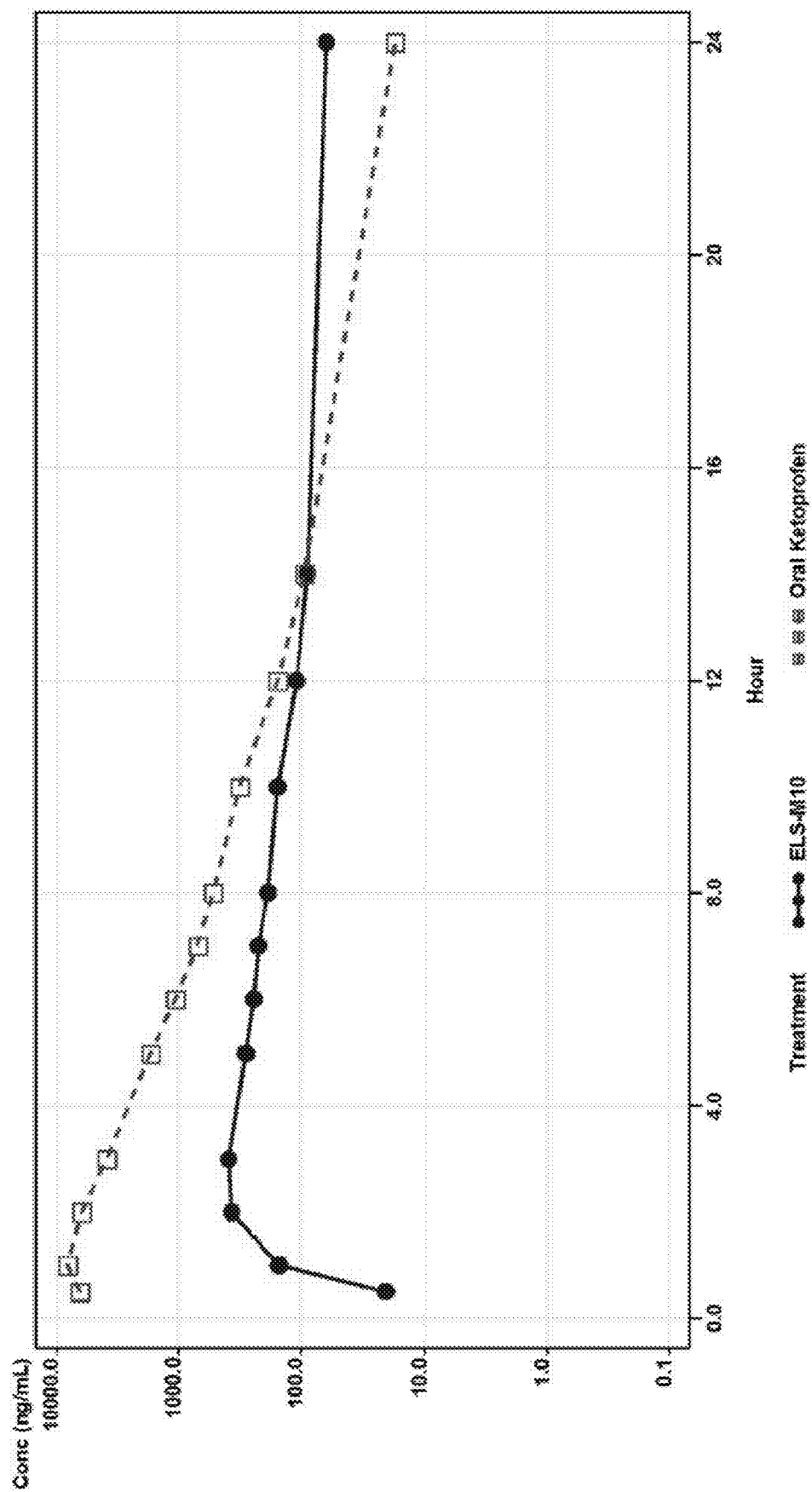

We have developed a composition including a gel dosage form of an NSAID (e.g., ketoprofen) for topical application for the acute treatment of migraine attacks in subjects with a history of migraine with or without aura. When used as a topical agent, the compositions of the invention exhibit relatively high NSAID drug penetration and bioavailability with non-significant skin irritation, sensitivity, and damage. The compositions of the invention provide a non-oral route of dosing that is particularly useful in patients who experience nausea (a common symptom associated with migraine). Furthermore, the compositions of the invention provide topical delivery as a clinically-desirable method of drug administration for migraine sufferers. Topical administration offers effective delivery of an NSAID for patients affected by migraine-related gastric stasis, nausea, or vomiting, any of which can limit or delay absorption of oral medication, and for subjects with an aversion to swallowing tablets.

Without wishing to be bound by theory, the compositions as described herein comprising an NSAID, when administered topically, can act via a peripheral mechanism, thus providing an opportunity to target peripheral receptors and neural pathways without systemic pain relief. Thus, the compositions of the invention are best suited for treating conditions associated with pain that affect localized superficial musculoskeletal soft tissues in areas that are accessible through topical delivery, such as the head, neck, shoulder, elbow, knee, hip, foot, or ankle. Accordingly, the present invention features a method for treatment and/or prevention of conditions associated with pain, migraine, and temporomandibular disorders by topically administering the compositions described herein.

Methods of Treatment

The present invention provides compositions that include an NSAID (e.g., aspirin, diclofenac, ibuprofen, ketoprofen, or naproxen, and/or salts thereof, enantiomers and racemic mixtures thereof) for both prophylactic and therapeutic treatments for alleviating conditions associated with pain (e.g., migraine). Specifically, the present invention relates to compositions of an NSAID (e.g., aspirin, diclofenac, ibuprofen, ketoprofen, or naproxen) that are formulated for topical administration and can be used to treat patients with acute pain, subacute pain, or chronic pain (e.g., pain that lasts longer than three to six months or pain that extends beyond the expected period of healing, and/or pain that originates from an initial trauma/injury or infection, or conditions associated with pain (e.g., post-herpetic neuralgia, trigeminal neuralgia, phantom limb pain, carpal tunnel syndrome, sciatica, pudendal neuralgia, complex regional pain syndrome, or central pain syndrome, headaches, in particular, migraine, joint pain, backaches, sinus pain, muscle pain, nerve pain, and pain affecting specific parts of the body, such as shoulders, pelvis, and neck, and/or pain that is associated with lower back pain, arthritis, headache, fibromyalgia, shingles, or nerve damage.

Inflammatory Pain

Inflammatory pain is a form of pain that is caused by tissue injury or inflammation (e.g., in postoperative pain or rheumatoid arthritis). Following a peripheral nerve injury, symptoms are typically experienced in a chronic fashion, distal to the site of injury and are characterized by hyperesthesia (enhanced sensitivity to a natural stimulus), hyperalgesia (abnormal sensitivity to a noxious stimulus), allodynia (widespread tenderness associated with hypersensitivity to normally innocuous tactile stimuli), and/or spontaneous burning or shooting lancinating pain. In inflammatory pain, symptoms are apparent, at least initially, at the site of injury or inflamed tissues and typically accompany arthritis-associated pain, musculo-skeletal pain, and postoperative pain. The different types of pain may coexist or pain may be transformed from inflammatory to neuropathic during the natural course of the disease, as in postherpetic neuralgia.

Other Types of Pain

Functional pain refers to conditions in which there is no obvious peripheral pathology or lesion to the nervous system. This particular form of pain is generated by abnormal function of the nervous system and conditions characterized by such pain include fibromyalgia, tension-type headache, and irritable bowel syndrome.

The pharmaceutical compositions and methods described herein may be useful for the treatment, reduction, or prevention of various forms of pain, namely inflammatory pain, nociceptive pain, and functional pain, whether acute or chronic. Exemplary conditions that may be associated with pain include, for example, soft tissue, joint, bone inflammation and/or damage (e.g., acute trauma, osteoarthritis, or rheumatoid arthritis), myofascial pain syndromes (fibromylagia), headaches (including cluster headache, migraine, and tension type headache), myocardial infarction, angina, ischemic cardiovascular disease, post-stroke pain, sickle cell anemia, peripheral vascular occlusive disease, cancer, inflammatory conditions of the skin or joints, diabetic neuropathy, and acute tissue damage from surgery or traumatic injury (e.g., burns, lacerations, or fractures).

The present invention may also be useful for the treatment or reduction of musculo-skeletal pain (after trauma, infections, and exercise), pain caused by spinal cord injury, tumors, compression, inflammation, dental pain, episiotomy pain, deep and visceral pain (e.g., heart pain, bladder pain, or pelvic organ pain), muscle pain, eye pain, orofacial pain (e.g., odontalgia, trigeminal neuralgia, glossopharyngeal neuralgia), abdominal pain, gynecological pain (e.g., dysmenorrhea and labor pain), pain associated with nerve and root damage due to trauma, compression, inflammation, toxic chemicals, hereditary conditions, central nervous system pain, such as pain due to spinal cord or brain stem damage, cerebrovascular accidents, tumors, infections, demyelinating diseases including multiple sclerosis, low back pain, sciatica, and post-operative pain.

Headaches

In one embodiment, the invention provides a method for treating headaches, including symptoms associated with headaches. The method involves topical administration of at least one therapeutic agent to the orbital foramen region of the patient. The orbital foramen region in mammals includes the notch of the eyebrow (or supraorbital foramen), which is an area where drugs in liquid formulation, as an ointment, as a gel, or as a cream formulation can penetrate into the regional arterial space and affect cerebral blood flow. The orbital foramen region also includes areas surrounding the supraorbital foramen, such as the base of the auriculotemporal branch of the trigeminal nerve or the auriculotemporal branch of the greater occipital nerve. These compositions may also be administered to the postauricular area, such as the area back of the ear; the forehead; or the either side of the head, such as on the left or right side of the scalp just above the ears, in the form of a liquid, ointment, gel, lotion, or patch. The pharmacokinetic properties of the composition are further described in the examples.

The methods and compositions of the invention can be used to treat a headache either by preventing the recurrence of a headache or by treating one or more symptoms associated with an established headache. The invention can be used to treat any type of headache, including a migraine headache, a tension headache, or a cluster headache. Symptoms and diagnosis of headaches can be readily determined by any parameters well known in the art, for example, as described in "The International Classification of Headache Disorders" (2d ed., ed. International Headache Society).

Exemplary symptoms of a migraine headache include: moderate to severe headache intensity; a unilateral headache; a headache with a pulsating or throbbing quality; a headache that worsens with physical activity; a headache that interferes with regular activities; nausea; vomiting; sensitivity to light, sound, or smell; depression; sleep disruption; ptosis; experiencing an aura, such as changes to vision; or paresthesia of the hand, arm, leg, or face.

The signs and symptoms of migraine vary among patients. Therefore, what a patient experiences before, during, and after an attack cannot be precisely defined. The four common phases of a migraine attack are listed below. However, the phases experienced and the symptoms experienced during those phases can vary from one migraine attack to another in the same migraineur (or migraine sufferer). These phases include: the prodrome phase, which occurs hours or days before the headache; the aura phase, which immediately precedes the headache; the pain phase, also known as headache phase; and the postdromal phase.

Symptoms within the prodromal phase include altered mood, irritability, depression or euphoria, fatigue, yawning, excessive sleepiness, craving for certain food (e.g., chocolate), stiff muscles (e.g., in the neck), constipation or diarrhea, increased urination, and other visceral symptoms. These symptoms usually precede the headache phase of the migraine attack by several hours or days, and experience teaches the patient or observant family how to detect that a migraine attack is near.

The aura phase comprises focal neurological phenomena that precede or accompany the attack. This phase typically appears gradually over 5 to 20 minutes and generally last fewer than 60 minutes. Symptoms of migraine aura can be visual, sensory, or motor in nature. Neurological symptoms during the visual aura phase include disturbance of vision (e.g., photopsia or scintillating scotoma, which is called "fortification spectra" or "teichopsia"); blurred or shimmering or cloudy vision; tunnel vision; and hemianopsia. Symptoms during the somatosensory aura phases include digitolingual or cheiro-oral paresthesias in the hand, in the arm, on the nose-mouth area on the same side; or on the face, lips and tongue. Other symptoms of the aura phase can include auditory or olfactory hallucinations, temporary dysphasia, vertigo, tingling or numbness of the face and extremities, and hypersensitivity to touch.

The pain phase usually begins within 60 minutes of the end of the aura phase, but can be delayed up to several hours, and it can be missing entirely. The typical migraine headache is unilateral, throbbing, and moderate to severe and can be aggravated by physical activity. Not all these features are necessary. The pain may be bilateral at the onset or start on one side and become generalized, and usually it alternates sides from one attack to the next. The onset is usually gradual. The pain peaks and then subsides and usually lasts 4 to 72 hours in adults and 1 to 48 hours in children. The frequency of attacks is extremely variable, from a few in a lifetime to several times a week, where the average migraineur experiences one to three headaches a month. The head pain varies greatly in intensity.

The pain of migraine is invariably accompanied by other features. Nausea occurs in about 18-40% of patients, and vomiting occurs in about one third of patients. Many patients experience sensory hyperexcitability manifested by photophobia, phonophobia, and osmophobia, where these patients typically seek a dark and quiet room. Typical symptoms include: blurred vision, nasal stuffiness, diarrhea, polyuria, pallor, sweating, localized edema of the scalp or face, scalp tenderness, prominence of a vein or artery in the temple, stiffness and tenderness of the neck, or impairment of concentration and mood are common. The extremities tend to feel cold and moist. Vertigo may be experienced; a variation of the typical migraine, called vestibular migraine, has also been described. Lightheadedness, rather than true vertigo, and a feeling of faintness may occur.

In the postdromal phase, the patient may feel tired or "hung-over" and have head pain, cognitive difficulties, gastrointestinal symptoms, mood changes, and weakness. Some people feel unusually refreshed or euphoric after an attack, whereas others note depression and malaise. Often, some of the minor headache phase symptoms may continue, such as loss of appetite, photophobia, and lightheadedness. For some patients, a 5- to 6-hour nap may reduce the pain, but slight headaches may still occur when the patient stands or sits quickly. These symptoms may go away after a good night's rest, although there is no guarantee. Some people may suffer and recover differently than others.

Tension type headaches (TTH) include those that are episodic or chronic. Both types of tension type headaches exhibit similar symptoms, where chronic TTH typically evolves from an episodic TTH. A chronic TTH typically lasts >15 days per month, where an episodic TTH typically lasts <15 days per month. Exemplary symptoms of chronic and episodic TTH include: headaches lasting from 30 minutes to 7 days; a nonpulsating feeling, such as pressing or tightening; mild or moderate intensity; bilateral location; lack of aggravation from routine physical activity; lack of nausea or vomiting; photophobia; or phonophobia.

A cluster headache is characterized as a trigeminal autonomic cephalgia. Exemplary symptoms include: severe or very severe unilateral orbital, supraorbital and/or temporal pain; ipsilateral conjunctival injection and/or lacrimation; ipsilateral nasal congestion and/or rhinorrhoea; ipsilateral eyelid edema; ipsilateral forehead and facial sweating; ipsilateral miosis and/or ptosis; or a sense of restlessness or agitation.

Temporomandibular Disorders (TMD)

The compositions of the invention are also useful for treating temporomandibular disorders (TMD). TMD occur as a result of problems with the jaw, jaw joint, and surrounding facial muscles that control chewing and moving the jaw. The temporomandibular joint (TMJ) is the hinge joint that connects the lower jaw (mandible) to the temporal bone of the skull, which is immediately in front of the ear on each side of the head. The joints are flexible, allowing the jaw to move smoothly up and down and side to side and enabling you to talk, chew, and yawn. Muscles attached to and surrounding the jaw joint control the position and movement of the jaw.

Because the compositions of the invention can be applied to the sternocleidomastoid muscle at the temporomandibular joint, it is within the scope of the invention that the composition will also be useful in treating TMD. The compositions of the invention when topically administered can alleviate one or more symptoms associated with TMD. People with TMD can experience severe pain and discomfort that can be temporary or last for many years. More women than men experience TMD, and TMD is seen most commonly in people between the ages of 20 and 40. The common symptoms of TMD include, but are not limited to:

Pain or tenderness in the face, jaw joint area, neck and shoulders, and in or around the ear when chewing, speaking, or opening the mouth wide Limited ability to open the mouth very wide Jaws that get "stuck" or "lock" in the open- or closed-mouth position Clicking, popping, or grating sounds in the jaw joint when opening or closing the mouth (which may or may not be accompanied by pain) or chewing A tired feeling in the face Difficulty chewing or a sudden uncomfortable bite—as if the upper and lower teeth are not fitting together properly Swelling on the side of the face May occur on one or both sides of the face Other common symptoms of TMD include pain in the temporomandibular joint or its surrounding tissues, functional limitations of the mandible, clicking in the temporomandibular joint during motion, toothaches, headaches, neck aches, dizziness, earaches, hearing problems, upper shoulder pain, and ringing in the ears (tinnitus).

Assessment of Efficacy

The compositions described herein can be tested for efficacy in any standard animal model of pain. Various models test the sensitivity of normal animals to intense or noxious stimuli (physiological or nociceptive pain). These tests include responses to thermal, mechanical, or chemical stimuli. Thermal stimuli usually involve the application of hot stimuli (typically varying between 42-55° C.) including, for example: radiant heat to the tail (the tail flick test), radiant heat to the plantar surface of the hind paw (the Hargreaves test), the hotplate test, and immersion of the hind paw or tail into hot water. Immersion in cold water, acetone evaporation, or cold plate tests may also be used to test cold pain responsiveness. Tests involving mechanical stimuli typically measure the threshold for eliciting a withdrawal reflex of the hind paw to graded strength monofilament von Frey hairs or to a sustained pressure stimulus to a paw (e.g., the Ugo Basile analgesiometer). The duration of a response to a standard pinprick may also be measured. When using a chemical stimulus, the response to the application or injection of a chemical irritant (e.g., capsaicin, mustard oil, bradykinin, ATP, formalin, acetic acid) to the skin, muscle joints or internal organs (e.g., bladder or peritoneum) is measured.

In addition, various tests assess pain sensitization by measuring changes in the excitability of the peripheral or central components of the pain neural pathway. In this regard, peripheral sensitization (i.e., changes in the threshold and responsiveness of high threshold nociceptors) can be induced by repeated heat stimuli as well as the application or injection of sensitizing chemicals (e.g., prostaglandins, bradykinin, histamine, serotonin, capsaicin, or mustard oil). Central sensitization (i.e., changes in the excitability of neurons in the central nervous system induced by activity in peripheral pain fibers) can be induced by noxious stimuli (e.g., heat), chemical stimuli (e.g., injection or application of chemical irritants), or electrical activation of sensory fibers.

In all of the above tests, outcome measures may be assessed, for example, according to behavior, electrophysiology, neurochemistry, or imaging techniques to detect changes in neural activity. In all of the above tests, an improvement in pain reduction can also be assessed by determining the pharmacological and non-pharmacological characteristics of pain such as pain intensity (as measured on a standardized pain scale), pattern (e.g., constant, intermittent), location, radiation, frequency, timing, and duration, impact on quality of life (sleep, function, appetite, and mood).

Therapeutic Agents

Suitable therapeutic agents or combinations thereof for use in the compositions and methods of the invention generally include those that will act locally to decrease painful vasodilatation of superficial cerebral arteries. For example, a therapeutic agent or combination thereof that provides an antihistaminic effect may do so in any number of ways, such as by H-1 receptor antagonism or by the release of histamine contained in mast cells that reside in the vicinity of the superficial cerebral arteries. Suitable therapeutic agents or combinations thereof also include, but are not limited to, those that inhibit the reuptake of norepinephrine from the nerve endings that surround the vasodilated cerebral artery; exhibit anti-cholinergic activity; provide local anesthetic activity; or have specific ion channel blocking activity, such as blocking sodium uptake and/or decrease the afferent activity of the nervous system or act functionally as non-steroidal anti-inflammatory drugs (by incorporation all drugs referred to as NSAIDS).

The methods and compositions of the invention typically utilize a therapeutic agent, either alone or in combination. Exemplary classes of therapeutic agents that may be used in the methods and/or compositions of the invention include an alpha adrenoceptor agonist; an anesthetic; an anticonvulsant; an anticholinergic compound; an antihistamine, including a tricyclic with antihistaminic activity; an anti-inflammatory compound, such as a cyclooxygenase (COX) inhibitor or a non-steroidal anti-inflammatory drug (NSAID); a beta receptor antagonist; an ion channel blocking compound (e.g., an analgesic), such as a sodium channel (e.g., Nav1.1, Nav1.2, Nav1.5, Nav1.6, or Nav.1.7) blocker or a calcium channel (L-, N-, P/Q-, T-, or R-calcium channel, or TRPV1-6 channels) blocker; a N-methyl d-aspartate (NMDA) receptor antagonist; a norepinephrine reuptake inhibitor; an opioid; a selective serotonin reuptake inhibitor; a serotonin agonist; a serotonin partial agonist; and/or a triptan. Preferred therapeutic agents to be formulated alone or in combination include: sumatriptan, ibuprofen, ketoprofen, diclofenac, dextromethorphan, gabapentin, amitriptyline, diphenhydramine, and doxepin.

Examples of alpha adrenoceptor agonists include phenylephrine, pseudoephedrine, and oxymetazoline. Examples of anesthetics include physostigmine, neostigmine, and procaine. Examples of anticonvulsants include gabapentin, topiramate, hydantoin, benzodiazepines, zonisamide, valproic acid, ethosuximide, carbamazepine, primidone, lamotrigine, felbamate, levetiracetam, and tiagabine. Examples of anticholinergic compounds include ipratropium bromide, oxitropium bromide, or tiotropium. Examples of antihistamines include carbinoxamine, clemastine, dimenhydrinate, pyrilamine, tripelennamine, chlorpheniramine, brompheniramine, hydroxyzine, cyclizine, acrivastine, cetririzine, azelastine, loratadine, fexofenadine, doxepin, diphenhydramine, and all tricyclics that have antihistaminic activity, such as amitriptyline, imipramine, promethazine, chlorpromazine, and nortriptyline.

Examples of anti-inflammatory compounds include aspirin, diclofenac, and COX inhibitors. Exemplary COX inhibitors include a non-selective COX inhibitor, such as an inhibitor for COX-1 and COX-2 or an inhibitor for COX and lipoxygenase (LOX); a selective COX-1 inhibitor; a selective COX-2 inhibitor (e.g., valdecoxib, rofecoxib, celecoxib, or any of the compounds described in U.S. Pat. No. 6,440,963, herein incorporated by reference); and/or a selective COX-3 inhibitor (e.g., paracetamol, phenacetin, antipyrine, or dipyrone). Examples of COX inhibitors include ibuprofen, including a racemic mixture or an enantiomer thereof; ketoprofen, including a racemic mixture or an enantiomer thereof; and/or naproxen.

Examples of beta receptor antagonists include propranolol, nadolol, timolol, pindolol, labetalol, metroprolol, atenalol, esmolol, and acebutolol. Examples of ion channel blocking compounds include flunarizine, verapamil, nifedipine, and nimodipine. Examples of NMDA receptor antagonists include dextromethorphan, ketamine, memantine, riluzole, and phencyclidine. Examples of norepinephrine reuptake inhibitor include reboxetine, duloxetine, and amitriptyline. Examples of opioids include morphine, codeine, meperidine, and oxycodone. Examples of triptans include almotriptan, eletriptan, frovatriptan, naratriptan, rizatriptan, sumatriptan, and zolmitriptan.

For those embodiments in which the composition is applied topically to the patient, the therapeutic agents used in the composition should have appropriate properties for topical administration. For example, suitable therapeutic agents for topical formulations include those that will act locally and upon absorption will be diluted into the large blood volume of the vascular space; or produce no adverse events. Suitable therapeutic agents and combinations are best administered in a non-greasy ointment or in a cream base.

Combinations of two or more therapeutic agents can be administered to a subject to treat a migraine headache. Exemplary combinations include a combination of an anti-inflammatory compound and an ion channel blocking compound, such as a COX-2 inhibitor and a calcium channel blocking compound; a combination of a COX inhibitor and an antihistamine; a combination of a general anti-inflammatory compound and an NMDA receptor antagonist; a combination of a triptan and a general anti-inflammatory compound; a combination of a triptan and an antihistamine; and a combination of a general anti-inflammatory compound and an opioid. In general, the following combinations would be useful for a migraine: muscle relaxants, such as anticonvulsants; opioids; analgesics, such as narcotic analgesics, opioids, NSAIDs, or COX inhibitors; NSAIDs; serotonergic agonists, such as a serotonin agonist or a serotonin partial agonist; COX-2 inhibitors; nitrates; beta blockers or beta receptor antagonist; anticonvulsants, such as hydantoin, benzodiazepines, or topiramate; alpha agonists or alpha adrenoceptor agonists; antihistamines; and local anesthetics.

Combination Therapy/Treatments

The compositions and methods of the invention can also be used in conjunction with other remedies known in the art that are used to treat pain including, corticosteroids, acetaminophen, opioids, muscle relaxants, anti-anxiety drugs, anti-depressants, anti-convulsant drugs, antipsychotics, mood stabilizers, lithium, and serotonin reuptake inhibitors (SSRIs). The compositions and methods of the invention can also be used in conjunction with other forms of treatment including but not limited to: cognitive-behavioral therapies, music therapies, art therapies, group therapies, psychotherapies, physical exercise, pet therapies, communication therapies, educational therapies, and family therapies. The choice of specific treatment may vary and will depend upon the severity of the pain, the subject's general health, and the judgment of the attending clinician.

The present compositions can also be formulated in combination with one or more additional active ingredients, which can include a pharmaceutical agent such NSAIDs (e.g., Aspirin (Anacin, Ascriptin, Bayer, Bufferin, Ecotrin, Excedrin), Choline and magnesium salicylates (CMT, Tricosal, Trilisate), Choline salicylate (Arthropan), Celecoxib (Celebrex), Diclofenac potassium (Cataflam), Diclofenac sodium (Voltaren, Voltaren XR), Diclofenac sodium with misoprostol (Arthrotec), Diflunisal (Dolobid), Etodolac (Lodine, Lodine XL), Fenoprofen calcium (Nalfon), Flurbiprofen (Ansaid), Ibuprofen (Advil, Motrin, Motrin IB, Nuprin), Indomethacin (Indocin, Indocin SR), Ketoprofen (Actron, Orudis, Orudis KT, Oruvail), Magnesium salicylate (Arthritab, Bayer Select, Doan's Pills, Magan, Mobidin, Mobogesic), Meclofenamate sodium (Meclomen), Mefenamic acid (Ponstel), Meloxicam (Mobic), Nabumetone (Relafen), Naproxen (Naprosyn, Naprelan*), Naproxen sodium (Aleve, Anaprox), Oxaprozin (Daypro), Piroxicam (Feldene), Rofecoxib (Vioxx), Salsalate (Amigesic, Anaflex 750, Disalcid, Marthritic, Mono-Gesic, Salflex, Salsitab), Sodium salicylate (various generics), Sulindac (Clinoril), Tolmetin sodium (Tolectin), Valdecoxib (Bextra)), corticosteroids (e.g., prednisolone, methylprednisolone, hydrocortisone, amcinonide, fluocinonide, flunisolide, prednicarbate, betamethasone, and triamcinolone acetonide), acetaminophen, opioids (e.g., morphine, fentanyl, oxcodone, codeine), muscle relaxants (e.g., carisoprodol, cyclobenzaprine, and diazepam), anti-anxiety drugs (e.g., duloxetine, fluoxetine, alprazolam, escitalopram, and lorazepam), anti-depressants (e.g., desipramine, amitriptyline, agomelatine, etoperidone, and phenelzine), anti-convulsant drugs (e.g., lithium carbonate, lithium citrate, topiramate, oxcarbazepine, and valproic acid), antipsychotics (e.g., aripiprazole, clozapine, risperidone, asenaphine, and olanzapine), and SSRIs (e.g., citalopram, paroxetine, fluvoxamine, and sertraline).

In one embodiment, any of the foregoing compounds may be formulated with an NSAID (e.g., aspirin, diclofenac, ibuprofen, ketoprofen, or naproxen) or administered along with an NSAID (e.g., aspirin, diclofenac, ibuprofen, ketoprofen, or naproxen) to a patient suffering from pain (e.g., pain associated with a migraine headache). When co-administered, the two compounds are desirably administered within 24 hours of each other (e.g., within 12 hours, 8 hours, 4, hours, 2 hours, 1 hour, 30 minutes, 15 minutes, or substantially simultaneously).

Dosing

The compositions of the invention may conveniently be administered in unit dosage form and may be prepared by any of the methods well-known in the pharmaceutical art, for example, as described in "Remington: The Science and Practice of Pharmacy" (20th ed., ed. A. R. Gennaro, 2000, Lippincott Williams & Wilkins). The concentration of at least one therapeutic agent in the formulation will vary depending upon a number of factors, including the dosage of the drug to be administered, and the route of administration.

A composition containing a therapeutic agent (e.g., ketoprofen) and a dermatologically acceptable excipient may be administered topically (e.g., to the trigeminal nerve area) in accordance with methods of the invention in an amount sufficient to provide 0.1 mg to 1000 mg (e.g., from 20 mg to 200 mg or, preferably, from 20 mg to 135 mg) of the therapeutic agent. The composition may contain from about 0.5% to about 5% by weight of the therapeutic agent.

The therapeutic agents may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

The composition can be prepared in any useful method. For example, at least one therapeutic agent is dissolved in ethanol and added to a mixture of polyethylene glycols (PEGs). In another example, the composition further includes a skin penetrating enhancer of a dimethyl alanine amide of medium chain fatty acids with carbon units varying between C-12 and C-16. More specifically, therapeutic agents alone or combinations thereof may be prepared in an ointment form or a cream form. In these forms, unit dispensing would be preferred, where the unit dosage of the therapeutic agent and vehicle would be in the range of 0.1 mg to 1000 mg and most preferred between 20 mg and 200 mg. For example, the dosages can contain from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient, from about 50 mg to about 300 mg, from about 50 mg to about 250 mg, from about 100 mg to about 300 mg, or, from about 100 mg to about 250 mg, from about 100 mg to about 500 mg, from about 500 mg to about 1000 mg of the active ingredient. In some embodiments, the dosage can represent a total maximum dose (e.g., a total maximum dose of 20 mg, a total maximum dose of 50 mg, a total maximum dose of 100 mg, or preferably a total maximum dose of 135 mg). In other embodiments, the dosage can represent a unit dose (e.g., a unit dose of 20, 20.5, 21, 21.5, 22, 22.5, 23, 23.5, 24, 24.5, 25, 25.5, 26, 26.5, 27, 27.5, 28, 28.5, 29, 29.5 mg, or preferably the unit dose is about 22.5 mg). In other embodiments, the unit dose can be applied or administered to achieve a total maximum daily dose. In preferred embodiments, a unit dose of 22.5 mg is administered to each side of the face to treat or prevent a head (e.g., a migraine headache) at least one time a day (one time, two times, three times, four times, or five times) for a total maximum dose of 45 mg, 90 mg, 135 mg, or 180 mg.

The therapeutic agent in this composition by weight would be in the range of 0.5% to 30% (w/w). The most preferred range would be between 0.5% and 5% (w/w). In another embodiment, the composition comprises between 0.5%-2%, 0.5%-3%, 0.5%-4%, 0.5%-5%, 0.5%-8%, 0.5%-10%, 1%-2%, 2.5%-5%, 8%-12%, 10/0-20%, or 20-30% (w/w) of at least one therapeutic agent. In one implementation, the therapeutic agent is present in the composition in an amount of at least 0.5%, at least 1%, at least 2%, at least 2.5%, at least 3%, at least 5%, at least 6%, at least 7%, at least 8%, at least 9%, at least 10%, at least 15%, at least 20%, or at least 25% (w/w), and may be, for example, ketoprofen or ibuprofen.

Optimization of the appropriate dosages can readily be made by the skilled practitioner in light of the pharmacokinetics of the therapeutic agent or combination of therapeutic agents used in the composition. Factors to be considered in setting dosages include the therapeutic agent's specific activity; the severity of the condition or symptoms of the subject; the age, condition, body weight, sex, and diet of the subject; the use (or not) of concomitant therapies; and other clinical factors.

Administration may be one or multiple times daily (e.g., two times, three times, up to four times a day), weekly (or at some other multiple day interval) or on an intermittent schedule, with that cycle repeated a given number of times (e.g., 2-10 cycles) or indefinitely. The compositions can be administered for at least two days (e.g., 2 days, 3, days, 4 days, 5 days, one week, or two weeks). The compositions may be administered as symptoms occur or until the symptoms subside. The compositions can also be administered chronically (e.g., more than twenty days, e.g., 21 days, 30 days, 60 days, 3 months, 6 months, 9 months, one year, two years, or three years). In one embodiment, the composition comprises between 1% to 30% (w/w) of at least one therapeutic agent (e.g., ketoprofen; gabapentin; dextromethorphan; a multi-mechanistic tricyclic molecule with activities including neurotransmitter uptake inhibition, antihistaminic or anticholinergic activity, such as imipramine, amitriptyline, and nortriptyline; or combinations thereof).

Formulations

The compositions can be formulated using any dermatologically acceptable carrier. Exemplary carriers include a solid carrier, such as alumina, clay, microcrystalline cellulose, silica, or talc; and/or a liquid carrier, such as an alcohol, a glycol, or a water-alcohol/glycol blend. The therapeutic agents may also be administered in liposomal formulations that allow therapeutic agents to enter the skin. Such liposomal formulations are described in U.S. Pat. Nos. 5,169,637; 5,000,958; 5,049,388; 4,975,282; 5,194,266; 5,023,087; 5,688,525; 5,874,104; 5,409,704; 5,552,155; 5,356,633; 5,032,582; 4,994,213; 8,822,537, and PCT Publication No. WO 96/40061. Examples of other appropriate vehicles are described in U.S. Pat. Nos. 4,877,805, 8,822,537, and EP Publication No. 0586106A1. Suitable vehicles of the invention may also include mineral oil, petrolatum, polydecene, stearic acid, isopropyl myristate, polyoxyl 40 stearate, stearyl alcohol, or vegetable oil.

The composition can further include a skin penetrating enhancer, such as those described in "Percutaneous Penetration enhancers", (eds. Smith E W and Maibach H I. CRC Press 1995). Exemplary skin penetrating enhancers include alkyl (N,N-disubstituted amino alkanoate) esters, such as dodecyl 2-(N,N dimethylamino) propionate (DDAIP), which is described in patent U.S. Pat. Nos. 6,083,996 and 6,118,020, which are both incorporated herein by reference; a water-dispersible acid polymer, such as a polyacrylic acid polymer, a carbomer (e.g., Carbopol™ or Carbopol 940P™, available from B. F. Goodrich Company (Akron, Ohio)), copolymers of polyacrylic acid (e.g., Pemulen™ from B. F. Goodrich Company or Polycarbophil™ from A. H. Robbins, Richmond, Va.; a polysaccharide gum, such as agar gum, alginate, carrageenan gum, ghatti gum, karaya gum, kadaya gum, rhamsan gum, xanthan gum, and galactomannan gum (e.g., guar gum, carob gum, and locust bean gum), as well as other gums known in the art (see for instance, Industrial Gums: Polysaccharides & Their Derivatives, Whistler R. L., BeMiller J. N. (eds.), 3rd Ed. Academic Press (1992) and Davidson, R. L., Handbook of Water-Soluble Gums & Resins, McGraw-Hill, Inc., N.Y. (1980)); or combinations thereof.

Other suitable polymeric skin penetrating enhancers are cellulose derivatives, such as ethyl cellulose, methyl cellulose, hydroxypropyl cellulose. Additionally, known transdermal penetrating enhancers can also be added, if desired. Illustrative are dimethyl sulfoxide (DMSO) and dimethyl acetamide (DMA), 2-pyrrolidone, N,N-diethyl-m-toluamide (DEET), 1-dodecylazacycloheptane-2-one (Azone™, a registered trademark of Nelson Research), N,N-dimethylformamide, N-methyl-2-pyrrolidone, calcium thioglycolate and other enhancers such as dioxolanes, cyclic ketones, and their derivatives and so on.

Also illustrative are a group of biodegradable absorption enhancers which are alkyl N,N-2-(disubstituted amino) alkanoates as described in U.S. Pat. Nos. 4,980,378 and 5,082,866, which are both incorporated herein by reference, including: tetradecyl (N,N-dimethylamino) acetate, dodecyl (N,N-dimethylamino) acetate, decyl (N,N-dimethylamino) acetate, octyl (N,N-dimethylamino) acetate, and dodecyl (N,N-diethylamino) acetate.

Particularly preferred skin penetrating enhancers include isopropyl myristate; isopropyl palmitate; dimethyl sulfoxide; decyl methyl sulfoxide; dimethylalanine amide of a medium chain fatty acid; dodecyl 2-(N,N-dimethylamino) propionate or salts thereof, such as its organic (e.g., hydrochloric, hydrobromic, sulfuric, phosphoric, and nitric acid addition salts) and inorganic salts (e.g., acetic, benzoic, salicylic, glycolic, succinic, nicotinic, tartaric, maleic, malic, pamoic, methanesulfonic, cyclohexanesulfamic, picric, and lactic acid addition salts), as described in U.S. Pat. No. 6,118,020; and alkyl 2-(N,N-disubstituted amino)-alkanoates, as described in U.S. Pat. Nos. 4,980,378 and 5,082,866.

The skin penetrating enhancer in this composition by weight would be in the range of 0.5% to 10% (w/w). The most preferred range would be between 1.0% and 5% (w/w). In another embodiment, the skin penetrating enhancer comprises between 0.5%-1%, 1%-2%, 2%-3%, 3%-4%, or 4%-5%, (w/w) of the composition.

The compositions can be provided in any useful form. For example, the compositions of the invention may be formulated as solutions, emulsions (including microemulsions), suspensions, creams, foams, lotions, gels, powders, or other typical solid, semi-solid, or liquid compositions (e.g., topical sprays) used for application to the skin or other tissues where the compositions may be used. The preferred compositions may also be applied as a patch, preferably to the postauricular area or on the neck just behind the ear. Such compositions may contain other ingredients typically used in such products, such as colorants, fragrances, thickeners (e.g., xanthan gum, a fatty acid, a fatty acid salt or ester, a fatty alcohol, a modified cellulose, a modified mineral material, Krisgel 100™, or a synthetic polymer), antimicrobials, solvents, surfactants, detergents, gelling agents, antioxidants, fillers, dyestuffs, viscosity-controlling agents, preservatives, humectants, emollients (e.g., natural or synthetic oils, hydrocarbon oils, waxes, or silicones), hydration agents, chelating agents, demulcents, solubilizing excipients, adjuvants, dispersants, skin penetrating enhancers, plasticizing agents, preservatives, stabilizers, demulsifiers, wetting agents, sunscreens, emulsifiers, moisturizers, astringents, deodorants, and optionally including anesthetics, anti-itch actives, botanical extracts, conditioning agents, darkening or lightening agents, glitter, humectants, mica, minerals, polyphenols, silicones or derivatives thereof, sunblocks, vitamins, and phytomedicinals.

The compositions can also include other like ingredients to provide additional benefits and improve the feel and/or appearance of the topical formulation. Specific classes of additives commonly use in these formulations include: isopropyl myristate, sorbic acid NF powder, polyethylene glycol, phosphatidylcholine (including mixtures of phosphatidylcholine, such as phospholipon G), Krisgel 100™, distilled water, sodium hydroxide, decyl methyl sulfoxide (as a skin penetrating enhancer), menthol crystals, lavender oil, butylated hydroxytoluene, ethyl diglycol reagent, and 95% percent (190 proof) ethanol.

Generally, the therapeutic agent when administered topically results in a peak plasma concentration that is lower than the peak plasma concentration of the same therapeutic agent when orally administered at about the same dosage (e.g., at about 130-150 mg of the therapeutic agent). The therapeutic agent when administered topically results in a peak plasma concentration at between two to three hours that is at most about 1100 ng/mL (e.g., 200 ng/mL, 250 ng/mL, 300 ng/mL, 350 ng/mL, 400 ng/mL, 420 ng/mL, 440 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1000 ng/mL, or 1050 ng/mL, and up to 1100 ng/mL). Preferably, the peak plasma concentration at three hours is about 440 ng/mL. The peak plasma concentrations of the topically administered therapeutic agent described herein are lower than the peak plasma concentrations of the same therapeutic agent when orally administered. Typically, the peak plasma concentration of an orally administered therapeutic agent (e.g., ketoprofen) is about 8000 ng/mL at one hour.

Furthermore, the therapeutic agent is administered in an amount such that the plasma concentration of the therapeutic agent (e.g., an NSAID, e.g., ketoprofen) ranges from about 50 ng/mL to about 150 ng/mL (e.g., about 50 ng/mL to about 75 ng/mL, about 50 ng/mL to about 100 ng/mL, about 50 ng/mL to about 125 ng/mL, about 80 ng/mL to about 100 ng/mL, about 90 ng/mL to about 100 ng/mL, about 105 ng/mL to about 115 ng/mL, about 105 ng/mL to about 120 ng/mL, about 110 ng/mL to about 120 ng/mL, about 120 ng/mL to about 130 ng/mL, about 130 ng/mL to about 145 ng/mL, about 145 ng/mL to about 150 ng/mL). The plasma concentration of the therapeutic agent is desirably maintained. The composition is formulated such that the therapeutic agent is released over an extended period of time, e.g., 2-24 hours or more (e.g., 2-4 hours, 2-8 hours, 2-10 hours, 2-15 hours, 2-20 hours, 4-8 hours, 4-10 hours, 4-20 hours, 8-10 hours, 8-15 hours, 10-15 hours, 15-20 hours, 20-25 hours), wherein the plasma concentrations may be maintained for up to 24 hours (e.g., up to 2 hours, up to 4 hours, up to 8 hours, up to 10 hours, up to 14 hours, up to 16 hours, up to 20 hours, up to 22 hours).

In particular embodiments, the compositions of the invention are formulated as described in U.S. Publication No. 2014-0088195 and International Publication No. WO 2014-052313, each of which is hereby incorporated by reference.

Route of Administration

The compositions can be administered in any number of ways. For example, the compositions in liquid form can be applied from absorbent pads; used to impregnate bandages and other dressings, directly onto the orbital foramen or surrounding areas of the subject (e.g., the mandibular junction and areas in close proximity to the trigeminal nerves). In another example, the composition in solid form, including semi-solid form, can be applied from a tube; or be applied directly onto the orbital foramen or surrounding areas of the subject. In yet another example, the composition in liquid form or solid form can be applied by using an applicator to spread the composition onto the orbital foramen region. The composition may also be applied to the skin under occlusive dressing in a dermal delivery system (e.g., a transdermal patch). The compositions can also be formulated as a topical spray for direct application onto the area to be treated.

Administration of therapeutic agents in controlled release formulations may be useful where the therapeutic agent has (i) a narrow therapeutic index (e.g., the difference between the plasma concentration leading to harmful side effects or toxic reactions and the plasma concentration leading to a therapeutic effect is small; (ii) a narrow slow absorption rate by or through the epithelium and/or dermis; or (iii) a short biological half-life, so that frequent dosing during a day is required in order to sustain a therapeutic level.

Many strategies can be pursued to obtain controlled release in which the rate of release outweighs the rate of metabolism of the therapeutic agent. For example, controlled release can be obtained by the appropriate selection of formulation parameters and ingredients, including, e.g., appropriate controlled release compositions and coatings. Examples include oil solutions, suspensions, emulsions, microcapsules, microspheres, nanoparticles, patches, and liposomes.

Further features and advantages of this invention are further illustrated by the following examples, which are in no way intended to be limiting thereof.

EXAMPLES

The following list of abbreviations and definitions of terms are used in the examples described hereafter.

| Abbreviation | Definition |
| --- | --- |
| ANCOVA | Analysis of Covariance |
| $AUC_{0-t}$ | area under the plasma concentration vs. time curve from time 0 (time of dosing) to the last time point with measurable drug concentration |
| $AUC_{0-inf}$ | area under the plasma concentration vs. time curve from time 0 to infinity |
| $AUC_{0-12}$ | area under the plasma concentration vs. time curve from time 0 to 12 hours post dose |
| $AUC_{0-24}$ | area under the plasma concentration vs. time curve from time 0 to 24 hours post dose |
| % $AUC_{extrap}$ | percent extrapolated AUC for $AUC_{0-inf}$ |
| BLQ | below the lower limit of quantitation |
| BMI | Body Mass Index |
| CI | confidence interval |
| $C_{max}$ | maximum observed concentration |
| CRF | case report form |
| CRU | clinical research unit |
| CV % | coefficient of variation (in percentage) |
| CYP | Cytochrome |
| GI | Gastrointestinal |
| GLSM | geometric least-squares mean |
| LLOQ | lower limit of quantitation |
| LSM | least-squares mean |
| $\lambda z$ | apparent first order elimination rate constant |
| UPLC/MS/MS | ultra performance liquid chromatography with tandem mass spectrometry |
| PAH | Pulmonary arterial hypertension |
| PK | pharmacokinetic(s) |

| Abbreviation | Definition |
|---|---|
| PPI | proton pump inhibitor |
| QC | quality control |
| SAS | Statistical Analysis System |
| SD | standard deviation |
| SR | sustained release |
| $t_{max}$ | time when $C_{max}$ occurred |
| $t_{1/2}$ | apparent elimination half life |

Materials and Methods
Material and HPLC Analysis

Ketoprofen was obtained from Boehinger-Ingelheim for preclinical work and obtained from COSMA S.p.A. for clinical work. An isocratic reversed-phase HPLC system was used to determine the stability and photostability of the ketoprofen formulations. The HPLC instrument was Agilent 1100. NovaPak® 4.6×300 mm C18 column from Waters was used. The mobile phase consisted of a mixture of formic acid buffer (0.025M) adjusted to pH 2.3 with hydrochloric acid and acetonitrile (50:50). The flow rate was 1.0 ml/min. Detection was accomplished at 220 nm and 254 nm. The volume of injection was set to 25 μl. Under these conditions, the retention times of ketoprofen and oxybenzone were approximately 5 min. and 13 min., respectively. The concentration ranges for the calibration curves of ketoprofen and oxybenzone were 7-210 μg/ml and 120-480 μg/ml, respectively. The run time for the samples was 20 min.

Example 1: Formulation Studies

A series of studies were conducted to find acceptable stabilizing polymer thickener(s) and to find the optimum levels of these polymers that would minimize freeze/thaw failure. The resulting formulations from these studies are presented below in Tables 1-8 and disclosed in International Publication No. WO/2014/052313, which is herein incorporated by reference in its entirety. Additional formulations are provided in U.S. Pat. Nos. 6,083,996 and 8,822,537, which are herein incorporated by reference in their entirety. The formulation used in the phase 1 clinical studies (ELS-M10) described below is a composition including 5% ketoprofen gel that delivers 135 mg ketoprofen per application and includes a higher concentration of free radical scavenger. In addition, to minimize the photosensitization effects of ketoprofen, the ELS-M10 formulation includes oxybenzone, a sunblocker. This formulation was used in permeation studies and toxicology studies (repeat dose dermal toxicity, photoallergy, and eye irritation). ELS-M10 is to be stored at 5° C. and is stable for 1 month. The ELS-M11 formulation described below and disclosed in International Publication No. WO/2014/052313 includes all of the components of the ELS-M10 formulation without the benzyl alcohol, which eliminates the irritation involved in topical application of the formulation. ELS-M11 was used in phase 2 clinical studies (see, Example 7) and registered under the trademark TOPOFEN™ (Trademark Application No. 86/447,026).

TABLE 1

Components of preferred compositions containing 10%, 5%, and 0.5% by weight ketoprofen.

| Component | w/w % | | |
|---|---|---|---|
| Ketoprofen, USP | 10 | 5 | 0.5 |
| Disodium EDTA, USP | 0.05 | 0.05 | 0.05 |
| Purified Water, USP | q.s. | q.s. | q.s. |
| Carbopol ® 980, NF | 0.5 | 0.5 | 0.5 |
| Carbopol ® Ultrez 10, NF | 1.25 | 1.25 | 1.25 |
| PEG-40 Hydrogenated Castor Oil, NF | 0.5 | 0.5 | 0.5 |
| Vitamin E USP | 0.05 | 0.05 | 0.05 |
| Ethyl Alcohol USP, anhydrous | 10 | 10 | 10 |
| Propylene glycol, USP | 10 | 10 | 10 |
| Isopropanol, USP | 9 | 10 | 10 |
| Isopropyl Myristate, USP | 3 | 3 | 3 |
| Benzyl Alcohol, NF | 1 | 1 | 1 |
| Oxybenzone, USP | 5 | 5 | 5 |
| Butylated Hydroxytoluene, NF | 1 | 1 | 1 |
| Triethanolamine | 1.5 | 1.5 | 1.5 |
| pH | 5 | 5 | 5 |

TABLE 2

Effects of Carbopol ® 980, Carbopol ® Ultrez 10, and Carbopol ® Ultrez 20 and combinations thereof on skin permeation.

| Ingredient | Composition (% w/w) | | | | |
|---|---|---|---|---|---|
| | Control | MRL-A | MRL-B | MRL-C | MRL-D |
| Ketoprofen | 5 | 5 | 5 | 5 | 5 |
| Carbopol ® Ultrez 10 NF | | 1.75 | | 0.75 | |
| Carbopol ® Ultrez 20 | | | 1.75 | | 0.75 |
| Carbopol ® 980 | 1.5 | | | 1 | 1 |
| Deionized Water | 58.73 | 52.15 | 52.15 | 52.15 | 52.15 |
| Disodium EDTA | 0.05 | 0.05 | 0.05 | 0.05 | 0.05 |
| Methylparaben, NF | 0.2 | 0 | 0 | 0 | 0 |
| Propylparaben, NF | 0.02 | 0 | 0 | 0 | 0 |
| Propylene glycol | | 10 | 10 | 10 | 10 |
| Isopropanol | | 10 | 10 | 10 | 10 |
| Cremophor 40[1] | | 0.5 | 0.5 | 0.5 | 0.5 |
| Oxybenzone | | 5 | 5 | 5 | 5 |
| BHT | | 1 | 1 | 1 | 1 |
| Vitamin E | | 0.05 | 0.05 | 0.05 | 0.05 |
| Isopropyl Myristate | 3 | 3 | 3 | 3 | 3 |
| Ethyl Alcohol USP, anh. | 30 | 10 | 10 | 10 | 10 |
| Triethanolamine, NF | 1.5 | 1.5 | 1.5 | 1.5 | 1.5 |

[1]PEG-40, Hydrogenated Castor Oil, NF.

All of the foregoing preparations showed similar permeation.

TABLE 3

Effect of Carbopol ® Ultrez 10 alone at the level of 1.75% w/w on skin permeation.

| Ingredient | Composition (% w/w) | |
|---|---|---|
| | Control | MRL-E |
| Ketoprofen | 5 | 10 |
| Carbopol ® Ultrez 10NF | | 1.75 |
| Carbopol ® 980 | 1.5 | |
| Deionized Water | 58.73 | 47.15 |
| Methyl paraben | 0.2 | |
| Propyl paraben | 0.02 | |
| Disodium EDTA | 0.05 | 0.05 |
| Propylene glycol | | 10 |
| Isopropanol | | 9 |
| Cremophor 40[1] | | 0.5 |
| Benzyl alcohol | | 1 |
| Oxybenzone | | 5 |
| BHT | | 1 |
| Vitamin E | | 0.05 |

TABLE 3-continued

Effect of Carbopol ® Ultrez 10 alone at the level of 1.75% w/w on skin permeation.

| Ingredient | Composition (% w/w) | |
|---|---|---|
| | Control | MRL-E |
| Isopropyl Myristate | 3 | 3 |
| Ethyl Alcohol USP, ahn. | 30 | 10 |
| Triethanolamine, NF | 1.5 | 1.5 |

PEG-40 Hydrogenated Castor Oil, NF.

The composition represented in Table 2 exhibited improved permeation after 4 hours and 22 hours.

TABLE 4

Effect of combination of Carbopol ® Ultrez 10 and Carbopol ® 980 on skin permeation.

| Ingredient | Composition (% w/w) | | | |
|---|---|---|---|---|
| | Control | MRL-F | MRL-G | MRL-H |
| Ketoprofen | 5 | 10 | 10 | 10 |
| Carbopol ® Ultrez 10 NF | | 0.25 | 0.75 | 0.5 |
| Carbopol ® 980 | 1.5 | 1.5 | 1 | 1.25 |
| Deionized Water | 58.73 | 46.15 | 46.15 | 46.15 |
| Disodium EDTA | 0.05 | 0.05 | 0.05 | 0.05 |
| Propylene glycol | | 10 | 10 | 10 |
| Isopropanol | | 10 | 10 | 10 |
| Cremophor 40[1] | | 0.5 | 0.5 | 0.5 |
| Benzyl alcohol | | 1 | 1 | 1 |
| Oxybenzone | | 5 | 5 | 5 |
| Methyl paraben | 0.2 | | | |
| Propyl paraben | 0.02 | | | |
| BHT | | 1 | 1 | 1 |
| Vitamin E | | 0.05 | 0.05 | 0.05 |
| Isopropyl Myristate | 3 | 3 | 3 | 3 |
| Ethyl Alcohol USP, anh. | 30 | 10 | 10 | 10 |
| Triethanolamine, NF | 1.5 | 1.5 | 1.5 | 1.5 |

[1]PEG-40 Hydrogenated Castor Oil.

The combination represented in Table 3 showed improved permeation compared to the control formulation. The ratio of the two polymers affects optimization of ketoprofen permeation.

TABLE 5

Permeation from larger (kg) batches using Carbopol ® 980/Carbopol ® Ultrez 10 ratio of 1%:0.75%.

| Ingredient | Composition (% w/w) | | |
|---|---|---|---|
| | MRL-I | MRL-J | MRL-K |
| Ketoprofen | 0 | 5 | 10 |
| Carbopol ® 980 | 1 | 1 | 1 |
| Carbopol ® Ultrez 10 NF | 0.75 | 0.75 | 0.75 |
| Deionized Water | 57.198 | 52.198 | 47.198 |
| Disodium EDTA | 0.05 | 0.05 | 0.05 |
| Propylene glycol | 10 | 10 | 10 |
| Isopropanol | 9 | 9 | 9 |
| Benzyl alcohol | 1 | 1 | 1 |
| Cremophor 40[1] | 0.5 | 0.5 | 0.5 |
| Oxybenzone | 5 | 5 | 5 |
| BHT | 1 | 1 | 1 |
| Vitamin E | 0.002 | 0.002 | 0.002 |
| Isopropyl Myristate | 3 | 3 | 3 |
| Ethyl Alcohol USP, anh. | 10 | 10 | 10 |
| Triethanolamine, NF | 1.5 | 1.5 | 1.5 |

[1]PEG-40 Hydrogenated Castor Oil.

The 10% cream had higher ketoprofen permeation at all time points.

TABLE 6

Effect of Carbopol ® Ultrez 10/Carbopol ® 980 ratios on skin permeation (100 gram batches).

| Ingredient | Composition (% w/w) | | |
|---|---|---|---|
| | Control | MRL-L | MRL-M |
| Ketoprofen | 5 | 10 | 10 |
| Carbopol ® Ultrez 10 NF | | 1.25 | 1.5 |
| Carbopol ® 980 | 1.5 | 0.5 | 0.25 |
| Deionized Water | 58.73 | 46.15 | 46.15 |
| Disodium EDTA | 0.05 | 0.05 | 0.05 |
| Propylene glycol | | 10 | 10 |
| Isopropanol | | 10 | 10 |
| Cremophor 40[1] | | 0.5 | 0.5 |
| Methyl paraben | 0.2 | | |
| Propyl paraben | 0.02 | | |
| Benzyl alcohol | | 1 | 1 |
| Oxybenzone | | 5 | 5 |
| BHT | | 1 | 1 |
| Vitamin E | | 0.05 | 0.05 |
| Isopropyl Myristate | 3 | 3 | 3 |
| Ethyl Alcohol USP, anh. | 30 | 10 | 10 |
| Triethanolamine, NF | 1.5 | 1.5 | 1.5 |

[1]PEG 40 Hydrogenated Castor Oil.

Good permeation was achieved with all preparations represented in Table 5. In general, relatively higher amounts of Carbopol® Ultrez 10 resulted in relatively higher ketoprofen permeation. The cosmetic appearance of the Carbopol® Ultrez 10 compositiosn also improved with higher amounts of the polymer present.

TABLE 7

Skin permeation from 1 kg batches with Carbopol ® Ultrez 10/Carbopol ® 980 ratio of 1.25%:0.5%.

| Ingredient | Composition (% w/w) | | |
|---|---|---|---|
| | Control | MRL-N | MRL-O |
| Ketoprofen | 5 | 5 | 10 |
| Carbopol ® Ultrez 10 NF | | 1.25 | 1.25 |
| Carbopol ® 980 | 1.5 | 0.5 | 0.5 |
| Deionized Water | 58.73 | 51.15 | 46.15 |
| Disodium EDTA | 0.05 | 0.05 | 0.05 |
| Propylene glycol | | 10 | 10 |
| Isopropanol | | 10 | 10 |
| Cremophor 40[1] | | 0.5 | 0.5 |
| Benzyl alcohol | | 1 | 1 |
| Methyl paraben | 0.2 | | |
| Propyl paraben | 0.02 | | |
| Oxybenzone | | 5 | 5 |
| BHT | | 1 | 1 |
| Vitamin E | | 0.05 | 0.05 |
| Isopropyl Myristate | 3 | 3 | 3 |
| Ethyl Alcohol USP, anh. | 30 | 10 | 10 |
| Triethanolamine, NF | 1.5 | 1.5 | 1.5 |

[1]PEG 40 Hydrogenated Castor Oil.

TABLE 8

Effect of Carbopol ® 980 and Carbopol ® Ultrez 10 ratios on skin permeation.

| Ingredient | Composition (% w/w) | | | |
|---|---|---|---|---|
| | Control | MRL-P | MRL-Q | MRL-R |
| Ketoprofen | 5 | 10 | 10 | 10 |
| Carbopol ® Ultrez 10 NF | | 1.25 | 1.25 | 1.25 |

TABLE 8-continued

Effect of Carbopol ® 980 and Carbopol ®
Ultrez 10 ratios on skin permeation.

| | Composition (% w/w) | | | |
|---|---|---|---|---|
| Ingredient | Control | MRL-P | MRL-Q | MRL-R |
| Carbopol ® 980 | 1.5 | 0.75 | 0.5 | 0.75 |
| Deionized Water | 58.73 | 45.9 | 41.15 | 40.9 |
| Disodium EDTA | 0.05 | 0.05 | 0.05 | 0.05 |
| Propylene glycol | | 10 | 10 | 10 |
| Isopropanol | | 10 | 10 | 10 |
| Cremophor 40[1] | | 0.5 | 0.5 | 0.5 |
| Benzyl alcohol | | 1 | 1 | 1 |
| Methyl paraben | 0.2 | | | |
| Propyl paraben | 0.02 | | | |
| Oxybenzone | | 5 | 5 | 5 |
| BHT | | 1 | 1 | 1 |
| Vitamin E | | 0.05 | 0.05 | 0.05 |
| Isopropyl Myristate | 3 | 3 | 3 | 3 |
| Ethyl Alcohol USP, anh. | 30 | 10 | 15 | 15 |
| Triethanolamine, NF | 1.5 | 1.5 | 1.5 | 1.5 |

[1]PEG 40 to Hydrogenated Castor Oil.

The results from these experiments indicated that the combination of a cross-linked polyacrylic acid interpolymer and a cross-linked polyacrylic acid homopolymer provides improved permeation of ketoprofen as compared to homopolymer only as the thickening agent.

Example 2: Pharmacokinetic Study Objectives and Endpoint

The primary objective of the Phase I study was to evaluate the relative bioavailability of ketoprofen following topical administration of a single dose (135 mg) of a gel formulation of ketoprofen (ELS-M10) compared to oral administration of a generic dose (150 mg) of ketoprofen. The secondary objectives included evaluating additional plasma ketoprofen pharmacokinetic (PK) parameter estimates following topical administration of a single dose of ELS-M10 compared to oral administration of a single dose of ketoprofen and evaluating the safety and tolerability of single doses of ELS-M10 in healthy volunteers.

The primary pharmacokinetic parameters used to assess the endpoints were:
the area under the plasma ketoprofen concentration vs. time curve from pre-dose to 24 hours post-dose, AUC (0-24),
the area under the plasma ketoprofen concentration vs. time curve from 0 hour to 12 hours post-dose, AUC (0-12),
and the first observed maximal plasma ketoprofen concentration, Cmax.

Secondarily, the safety parameters were assessed as follows:
adverse events (AEs)
and absolute and changes over time for hematology, clinical chemistry, urinalysis, and vital signs (blood pressure (BP) and heart rate (HR)).

Other pharmacokinetic parameters and endpoints included:
the area under the plasma ketoprofen concentration vs. time curve from time of dosing (0 hour) to infinity, AUC(0-inf)
plasma ketoprofen concentration vs. time data, the area under the plasma ketoprofen concentration vs. time curve from time of dosing (0 hour) to the last time point with measurable ketoprofen concentration, AUC(0-t),
the apparent plasma half-life, $t_{half}$,
and the percentage of AUC(0-inf) that is extrapolated, % AUCextrap.

Example 3: Phase 1 Study Design and Study Population

The Phase 1 study was a single center, randomized, crossover, open-label study to evaluate the pharmacokinetics, safety, and tolerability of single maximal doses of ELS-M10 and oral ketoprofen in a total of 20 healthy males or nonpregnant, nonlactating, healthy females between 18 and 50 years of age (inclusive) with a body mass index (BMI) in the range of 19 to 28 (inclusive).

During the Treatment Period, at Visit 2 and Visit 3, a single dose of study medication was administered before a standardized breakfast. Subjects were randomized in a 1:1 ratio to receive one of the following two treatment sequences:
ELS-M10 gel containing 135 mg of ketoprofen (as a topical application of 2.7 g gel) at Visit 2 (Day 1), followed by ketoprofen 150 mg (administered orally as two 75 mg capsules) at Visit 3 (Day 4),
Ketoprofen 150 mg (administered orally as two 75 mg capsules) at Visit 2 (Day 1), followed by ELS-M10 gel containing 135 mg of ketoprofen (topical) at Visit 3 (Day 4).

Figure 14:
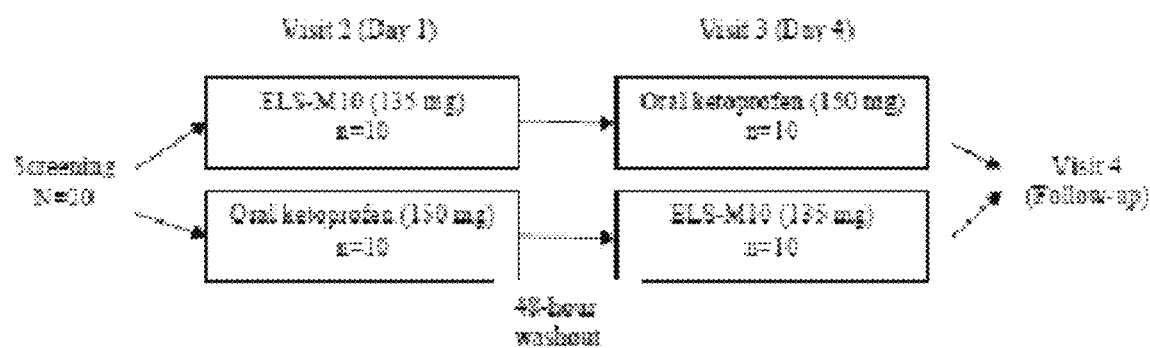
FIG. 14 is flowchart depicting the study design used in the assessment of ELS-M10 gel.

Subjects completed a 48-hour washout period between the first and second treatments. The study design is depicted graphically in FIG. 14. Subjects considered to have completed the study were those who had completed all study assessments. All subjects who completed the study assessments returned one week after treatment to complete additional safety and clinical laboratory assessments.

During the study, blood sampling occurred at specific times. The Plasma Concentration Population included all subjects in the Safety Population who had valid plasma ketoprofen concentration data. Five subjects experiencing burning and erythema at the ELS-M10 gel application site were removed from summary analyses.

The Pharmacokinetic Parameter Population included all subjects in the Plasma Concentration Population who had adequate plasma ketoprofen concentration data for the calculation of pharmacokinetic parameters in any of the treatment and dosing periods. Five subjects experiencing burning and erythema at the gel application site were removed from summary analyses.

A total of 20 subjects (11 males and 9 females) were enrolled in the study. The ages of the enrolled subjects ranged from 18-50 (median: 37.3) years, and BMIs ranged from 19.0-31.0 (mean: 25.7) kg/m².

Example 4: Pharmacokinetic Methodology

The maximum amount of ELS-M10, a topical gel containing 5% ketoprofen, was administered topically to the subject's face in a single dose of 135 mg of ketoprofen. Site personnel applied 2.7 mL of ELS-M10 gel before a standardized breakfast.

Oral ketoprofen was supplied as the commercially-available, 75 mg capsules manufactured by Teva Pharmaceuticals USA. Subjects took two 75 mg capsules (total dose 150 mg) before a standardized breakfast.

Before the initiation of any medications, the investigator reviewed the approved local labeling for the medication selected to determine if there were any restrictions or adjustments to dosing. During the study, subjects did not receive:

- NSAIDs, including aspirin
- Tiaprofenic acid, suprofen, fenofibrate, oxybenzone, or octocrylene (e.g., sunscreen, make up)
- Herbal preparations (e.g., feverfew, butterbur) for migraine prophylaxis.
- Monoamine oxidase inhibitors and tricyclic amines
- Niacin (except as part of routine vitamin supplementation)
- Potent inducers of CYP3A4 (including St John's Wort, rifampicin, carbamazepine, and phenytoin)
- Erythropoietin
- Hypertension treatments including ACE inhibitors such as benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik); diuretics ('water pills')
- Lithium (Eskalith, Lithobid)
- Medications for diabetes
- Methotrexate (Rheumatrex)
- Phenytoin (Dilantin)
- Probenecid (Benemid)
- Sulfa antibiotics such as sulfisoxazole (Gantrisin) and sulfamethoxazole (in Bactrim, in Septra)
- Any prescription or OTC drug in a cream or ointment vehicle
- Corticosteroids The use of dietary/herbal products during the trial was permitted. The Investigator exercised medical judgment to decide if non-prescription OTC medications and/or vitamins could potentially affect a subject's response with respect to the study endpoints or participation in the study. If these compounds had such potential, then they were discontinued. Subjects were randomized in a 1:1 ratio to receive one of the following two treatment sequences:

- ELS-M10 gel containing 135 mg of ketoprofen (topical) at Visit 2 (Day 1), followed by ketoprofen 150 mg (administered orally as two 75 mg capsules) at Visit 3 (Day 4),
- Ketoprofen 150 mg (administered orally as two 75 mg capsules) at Visit 2 (Day 1), followed by ELS-M10 gel containing 135 mg of ketoprofen (topical) at Visit 3 (Day4).

Subjects were required to report to the clinical site at 7 am in a fasted state on the mornings of Visit 2 and Visit 3, and remained at the site until at least 24 hours post-dosing. On arrival, subjects completed all pre-dose assessments, including vital signs assessment and PK sampling, and received their scheduled treatment. Subjects had breakfast after dosing and prior to the 0.5 hour post-dose PK sample. Subjects remained in the clinic until after collection of the 24-hour post-dose PK sample. Standard meals (breakfast, lunch, snack, and dinner) were provided during confinement at the clinical center. Aside from the inclusion and exclusion criteria, subjects agreed to abide by each of the following restrictions for the specified time:

- Subjects were not allowed to take recreational drugs during the entire trial.
- Subjects were required to abstain from alcohol for 48 hours prior to admission to the clinical center and before each study visit. Abstinence was confirmed with an alcohol test at admission to each visit.
- Subjects were required to fast for 10 hours prior to administration of the trial medication.
- At all times, water was permitted ad libitum.
- Subjects were required to abstain from blood donation during the entire duration of the trial.

The primary assessment is the PK profile of each dosage form of ketoprofen. Plasma PK samples were obtained from all study subjects according to the schedule listed in Table 9. A vital signs assessment (heart rate and BP) was performed on all study subjects prior to the PK blood draw.

TABLE 9

Pharmacokinetic Sampling Time Points

| Assessment | Time (hr) | | | | | | | | | | | | |
|---|---|---|---|---|---|---|---|---|---|---|---|---|---|
| | $0^1$ | 0.5 | 1 | 2 | 3 | 5 | $6^2$ | 7 | 8 | 10 | 12 | 14 | 24 |
| PK sample | X | X | X | X | X | X | X | X | X | X | X | X | X |
| Vital signs assessment | X | | X | | X | | | | X | | X | | X |

[1]Collect sample within 30 minutes prior to dose administration.
[2]The 6-hour sample is to be taken immediately after removal of the gel from the subject's face.

At each sampling time point, whole blood (approximately 2.0 mL/sample) was collected into pre-chilled blood collection tubes containing K2EDTA. Blood samples were kept on wet ice until centrifugation within 1 hour of collection. Blood samples were spun in a refrigerated centrifuge at 4° C. (approximately 3000 rpm for ~10 minutes) to separate the plasma. After centrifugation, harvested plasma (no more than 800 μL) was immediately transferred to a pre-chilled (refrigerated), pre-labeled tube (provided by AIT Bioscience) containing 12 mg of citric acid. The tubes were mixed well until the citric acid was completely dissolved and immediately transferred to storage at ~70° C. until shipment to AIT Biosciences. Plasma ketoprofen concentrations were determined under the direction of AIT Bioscience (Indianapolis, Ind.) using a validated analytical method.

Example 5: Pharmacokinetic Statistical Analysis

The plasma concentration population included all subjects who received a dose of study drug and had valid ketoprofen concentration data. The pharmacokinetic parameter population included all subjects in the plasma concentration population who had adequate plasma ketoprofen concentration data for the calculation of PK parameters during any of the time periods.

Plasma concentration data of ketoprofen is listed by subject, period, treatment, nominal sampling time, and actual sampling time, along with calculated elapsed time and summarized by treatment and nominal time. Standard summary statistics were calculated for concentrations at each time point, applying methods described in the Statistical Analysis Plan (SAP). Mean and median plasma ketoprofen concentration vs. time data were plotted on a linear scale using nominal time overlaying the two treatments in one plot. Figures of linear and semi-logarithmic plots were generated for individual subject plasma concentration vs. time data overlay the two treatments using the actual sampling times.

Pharmacokinetic parameters of ketoprofen were derived from individual plasma concentration vs. time data by noncompartmental methods using WinNonlin Professional Edition version 5.2.1 or above (Pharsight Corporation, Mountain View, Calif., USA). Actual times were used to estimate the individual plasma pharmacokinetic parameters. The following pharmacokinetic parameters were calculated as described in Table 10:

TABLE 10

| Pharmacokinetic parameters | |
|---|---|
| $C_{max}$ (ng/mL) | the first observed maximum plasma concentration |
| $t_{max}$ [hr(s)] | the time after dosing at which $C_{max}$ is observed |
| $AUC_{0-t}$ (hr * ng/mL) | area under the plasma concentration-time curve from time zero (i.e., time of dosing) to the last time point with measurable drug concentration ($t_{last}$), as calculated by linear trapezoidal method |
| $AUC_{0-12}$ (hr * ng/mL) | area under the plasma concentration-time curve from time zero (i.e., time of dosing) to 12 hours post dose, as calculated by linear trapezoidal method, |
| $AUC_{0-24}$ (hr * ng/mL) | area under the plasma concentration-time curve from time zero (i.e., time of dosing) to 24 hours post dose, as calculated by linear trapezoidal method |
| $\lambda_z$, $hr^{-1}$ or 1/hr | apparent first order elimination rate constant, determined (if data permit) from the slope of the apparent terminal log-linear phase of the plasma concentration vs. time curve using at least three time points |
| $t_{1/2}$ (hr) | apparent plasma elimination half-life calculated (if data permit) as $\ln 2/\lambda_z$ |
| $AUC_{0-inf}$ (hr * ng/mL) | area under the plasma concentration vs. time curve extrapolated to infinity, where data permit, calculated as the sum of $AUC(0_t)$ $C_{last}/\lambda_z$, where $C_{last}$ is the plasma concentration at $T_{last}$ |
| % $AUC_{extrap}$ | the percentage of $AUC_{0-inf}$ obtained by extrapolation beyond the last time point with measurable plasma concentration, calculated as 100% × $[AUC_{0-inf} - AUC_{0-t}]/AUC_{0-inf}$ |

Twenty subjects were randomized to ensure 18 subjects would complete the study, assuming a 10% drop-out rate. The sample size was based on variability ranges and confidence interval (CI) half widths that allowed adequate proof that systemic exposure for ELS-M10 (135 mg) would not greatly exceed that of oral ketoprofen (150 mg).

Using variability estimates that represented up to a coefficient of variance (CV %) of 80%, 18 subjects would give a 90% CI half width of 0.4 with 95% probability when evaluating the difference in treatment means of log-transformed maximum plasma concentration (Cmax), area under the plasma concentration vs. time curve (AUC) from time 0- to 24-hours post-dose (AUC(0-24)), or AUC from time 0 to 12 hours post-dose AUC(0-12).

If the CV % is closer to 100%, then a CI half width of 0.6 can be produced with 95% probability. If the exposure of ELS-M10 is less than 60% of that of oral ketoprofen, then the upper limit of the 90% CI may still be less than 1.25 with respect to the ratio of the two treatments.

A total of 20 subjects (11 males and 9 females) were enrolled in the study. The ages of the enrolled subjects ranged 18-51 (mean: 31.3) years, and BMIs ranged 19.0-34.0 (mean: 24.6) kg/m2. Subjects 2, 3, 7, 14, and 16 had reduced exposure to ELS-M10 since the gel was removed within the hour following application due to burning and erythema. These subjects were removed from the primary summary analyses. Eighteen subjects completed the study. Two subjects elected to leave the study due to family/business conflicts. The analysis sets for the pharmacokinetics study is displayed in Table 11 below.

TABLE 11

| Analysis Sets | | |
|---|---|---|
| Analysis Set | Treatment | Number Evaluated |
| Pk Concentration | ELS-M10 | 15 (75%) |
| | Oral Ketoprofen | 20 (100%) |
| PK Parameter | ELS-M10 | 15 (75%) |
| | Oral Ketoprofen | 20 (100%) |

TABLE 11-continued

| Analysis Sets | | |
|---|---|---|
| Analysis Set | Treatment | Number Evaluated |
| Early Removal Pk Concentration | ELS-M10 | 5 (25%) |
| | ELS-M10 | 5 (25%) |

Plasma concentration data of Ketoprofen, along with dosing date/time, sampling date/time, and the calculated actual sampling time for individual subjects are presented in Table 12. Study subjects were sampled at the planned times with sample time deviations ranging from −2 min to +5 min. Subject 9 exceeded the planned sample time by 12 minutes at the 3-hr mark and 16 minutes at the 6-hr mark. Five subjects during the ELS-M10 treatment had a premature treatment withdrawal by removing the gel at time less than an hour due to skin irritation. These subjects were not included in the summaries (unless otherwise specified). Mean and median plasma ketoprofen concentration vs. time profiles following administration are depicted in FIGS. 1A and 1B and FIGS. 2A and 2B, respectively, as linear-linear and log-linear plots.

The summary statistics of PKad parameter estimates by treatment are presented in Table 13. Note that this table does not include data for the five subjects who were removed early from the study. Additionally, one subject had $R^2$ values too low for reliable calculation of half-life and AUC(inf). Individual plots of the PK parameters (spaghetti plots) are seen in FIGS. 3-7.

TABLE 12

Ketoprofen plasma concentrations (ng/mL)

| Hour | Treatment | N | Mean | Median | STD | Min | Max |
|---|---|---|---|---|---|---|---|
| 0.0 | ELS-M10 | 15 | 0.2 | 0.0 | 0.431 | 0 | 1 |
| | Oral Ketoprofen | 20 | 0.5 | 0.0 | 0.876 | 0 | 3 |
| 0.5 | ELS-M10 | 15 | 38.7 | 20.9 | 42.605 | 2 | 153 |
| | Oral Ketoprofen | 20 | 8071.3 | 6545.0 | 6442.8 | 152 | 19700 |
| 1.0 | ELS-M10 | 15 | 213.8 | 154.0 | 207.60 | 14 | 718 |
| | Oral Ketoprofen | 20 | 8102.4 | 8180.0 | 3902.1 | 377 | 13800 |
| 2.0 | ELS-M10 | 15 | 433.9 | 366.0 | 281.83 | 125 | 1050 |
| | Oral Ketoprofen | 20 | 634.0 | 6350.0 | 1729.1 | 2720 | 9370 |
| 3.0 | ELS-M10 | 15 | 442.1 | 391.0 | 233.67 | 197 | 930 |
| | Oral Ketoprofen | 20 | 4414.6 | 3960.0 | 2360.3 | 322 | 9310 |
| 5.0 | ELS-M10 | 15 | 321.6 | 285.0 | 132.03 | 179 | 666 |
| | Oral Ketoprofen | 20 | 2177.4 | 1725.0 | 1623.8 | 235 | 6700 |
| 6.0 | ELS-M10 | 15 | 286 | 246.0 | 112.88 | 160 | 565 |
| | Oral Ketoprofen | 20 | 1310.8 | 1085.0 | 977.08 | 222 | 4440 |
| 7.0 | ELS-M10 | 15 | 241.1 | 222.0 | 89.957 | 124 | 423 |
| | Oral Ketoprofen | 20 | 873.3 | 711.5 | 616.51 | 174 | 2520 |
| 8.0 | ELS-M10 | 15 | 208.4 | 187.0 | 76.892 | 120 | 355 |
| | Oral Ketoprofen | 20 | 632.3 | 524.0 | 435.36 | 112 | 1870 |
| 10.0 | ELS-M10 | 15 | 165.2 | 156.0 | 60.140 | 94 | 299 |
| | Oral Ketoprofen | 20 | 364.2 | 320.5 | 242.98 | 61 | 945 |
| 12.0 | ELS-M10 | 15 | 122.1 | 110.0 | 45.386 | 68 | 229 |
| | Oral Ketoprofen | 20 | 203.7 | 156.0 | 152.04 | 31 | 610 |
| 14.0 | ELS-M10 | 15 | 99.8 | 89.8 | 33.390 | 54 | 177 |
| | Oral Ketoprofen | 20 | 120.2 | 96.2 | 94.955 | 20 | 399 |
| 24.0 | ELS-M10 | 15 | 60.8 | 62.5 | 28.824 | 7 | 109 |
| | Oral Ketoprofen | 20 | 19.8 | 17.3 | 14.849 | 6 | 70 |

TABLE 13

Summary of Pharmacokinetic Parameters

| Variable | Treatment | N | Geo. Mean | % CVb | Arith. Mean | STD | Median | Min | Max |
|---|---|---|---|---|---|---|---|---|---|
| Half-life | ELS-M10 | 14 | — | — | 10.22 | 3.60 | 9.73 | 3.7 | 19.2 |
| | Oral Ketoprofen | 20 | — | — | 3.71 | 0.57 | 3.75 | 2.9 | 5.2 |
| AUC(0-12) | ELS-M10 | 15 | 2809.3 | 45 | 3070.8 | 1384. | 2960.7 | 1483 | 6164 |
| | Oral Ketoprofen | 20 | 28438.6 | 32 | 29634.5 | 8181. | 27574.1 | 11654 | 44839 |
| AUC(0-24) | ELS-M10 | 15 | 3765.3 | 40 | 4037.3 | 1592. | 4044.5 | 2212 | 7370 |
| | Oral Ketoprofen | 20 | 29222.5 | 32 | 30456.8 | 8442. | 28333.5 | 12041 | 46748 |
| AUC(all) | ELS-M10 | 15 | 3766.2 | 40 | 4038.3 | 1592. | 4060.2 | 2212 | 7370 |
| | Oral Ketoprofen | 20 | 29223.0 | 32 | 30457.6 | 8443. | 8443.03 | 12041 | 46754 |
| AUC(0-inf) | ELS-M10 | 14 | 4652.9 | 38 | 4944.8 | 1792. | 4687.4 | 2638 | 8201 |
| | Oral Ketoprofen | 20 | 29321.4 | 32 | 30561.7 | 8479. | 8478.81 | 12086 | 46940 |
| AUC(0-t) | ELS-M10 | 15 | 3766.2 | 40 | 4038.3 | 1592. | 4060.2 | 2212 | 7370 |
| | Oral Ketoprofen | 20 | 29223.0 | 32 | 30457.3 | 8443. | 28334.6 | 46754 | 46754 |
| $C_{max}$ | ELS-M10 | 15 | 416.8 | 58 | 478.7 | 273. | 391.0 | 197 | 1050 |
| | Oral Ketoprofen | 20 | 9689.6 | 44 | 10558.0 | 4700. | 9640.0 | 5440 | 19700 |
| $T_{max}$ | ELS-M10 | 15 | — | — | 3.0 | | 3.00 | 2.0 | 5.0 |
| | Oral Ketoprofen | 20 | — | — | 0.5 | | 1.00 | 0.5 | 5.0 |

Table 14, below, summarizes the relative bioavailability of ELS-M10 ketoprofen to oral ketoprofen.

TABLE 14

Summary ANOVA Results of Treatment Comparison

| Parameter | Treatment | Ratio | Lower 90% CL | Upper 90% CL |
|---|---|---|---|---|
| AUC (0-12) | ELS-M10 vs. Oral Ketoprofen | 0.10 | 0.08 | 0.12 |
| AUC (0-24) | ELS-M10 vs. Oral Ketoprofen | 0.13 | 0.11 | 0.15 |
| AUC (inf) | ELS-M10 vs. Oral Ketoprofen | 0.16 | 0.14 | 0.19 |
| $C_{max}$ | ELS-M10 vs. Oral Ketoprofen | 0.04 | 0.03 | 0.116 |

Following drug administration after consuming a standardized well-balanced meal, the ELS-M10 ketoprofen treatment concentrations were >20.9 ng/mL in plasma at the first sampling time (0.5 hour post dose), while the oral ketoprofen treatment had most subjects with concentration levels >6545 ng/mL at the first sampling time point. All subjects reached maximum concentrations by five hours with median times of three hours for ELS-M10 and one hour for oral ketoprofen. All treatments had ketoprofen concentration levels <110 ng/mL by 24 hours.

Maximum concentrations were higher for all subjects when treated with oral ketoprofen versus being topically treated with ELS-M10 ketoprofen. Maximum mean exposure of ELS-M10 ketoprofen was estimated as 4% of oral ketoprofen (ratio 90% CI of 0.03 to 0.11) with geometric means of 417 ng/mL versus 9690 ng/mL. The overall range of the maximum concentration of ELS-M10 ketoprofen was 197 ng/mL to 1050 ng/mL. The overall range of the maximum concentration for oral ketoprofen ranged from 5440 ng/mL to 19700 ng/mL.

Ketoprofen half-life for ELS-M10 was substantially longer than for oral ketoprofen (mean(std) of 10.22(3.60) hours versus 3.17(0.57) hours). Overall exposure of ELS-M10 ketoprofen, as measured by AUC(0-inf), was estimated to be 16% (ratio 90% CI of 0.14 to 0.19) of the oral ketoprofen treatment (geometric mean (% CVb) of 4653 ng/mL (38%) versus 29321 ng/mL (32%)).

Approximately 60% of the total ketoprofen exposure was attained in the first 12 hours for ELS-M10 as shown by AUC(0-12) data versus AUC(0-inf) data. ELS-M10 mean ketoprofen twelve hour exposure (AUC(0-12)) and ELS-M10 mean ketoprofen exposure over the sampling time AUC(0-24), were estimated as 13% (ratio 90% CI of 0.11 to 0.15) and 10% (ratio 90% CI of 0.08 to 0.12), respectively, of the oral ketoprofen.

Figure 3:
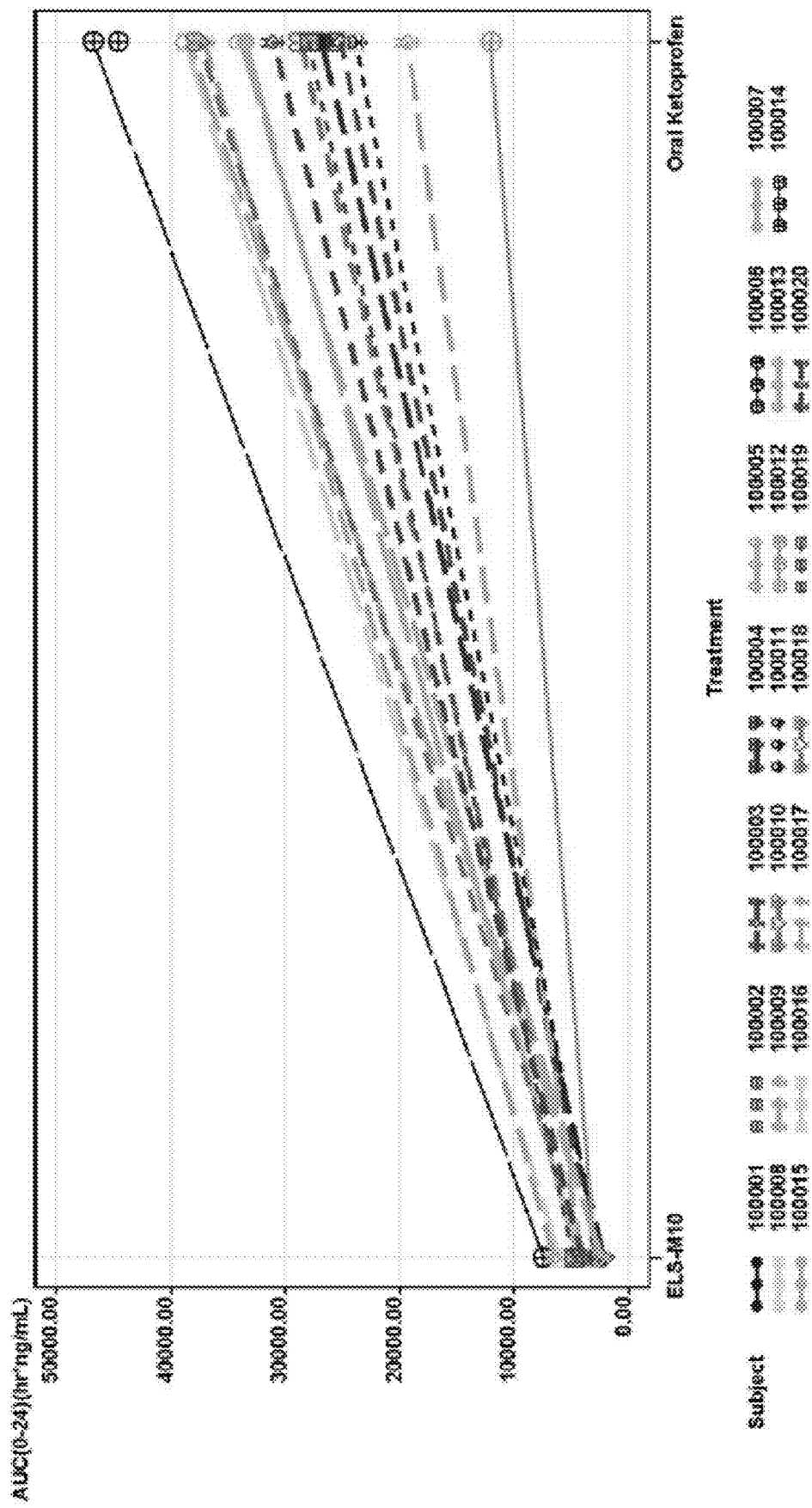
FIG. 3 is a plot of individual ketoprofen AUC(0-24) (area under plasma concentration vs. time curve from time 0 (i.e., time of dosing) to 24 hours post dose, calculated by linear trapezoidal method) across treatments.
Figure 4:
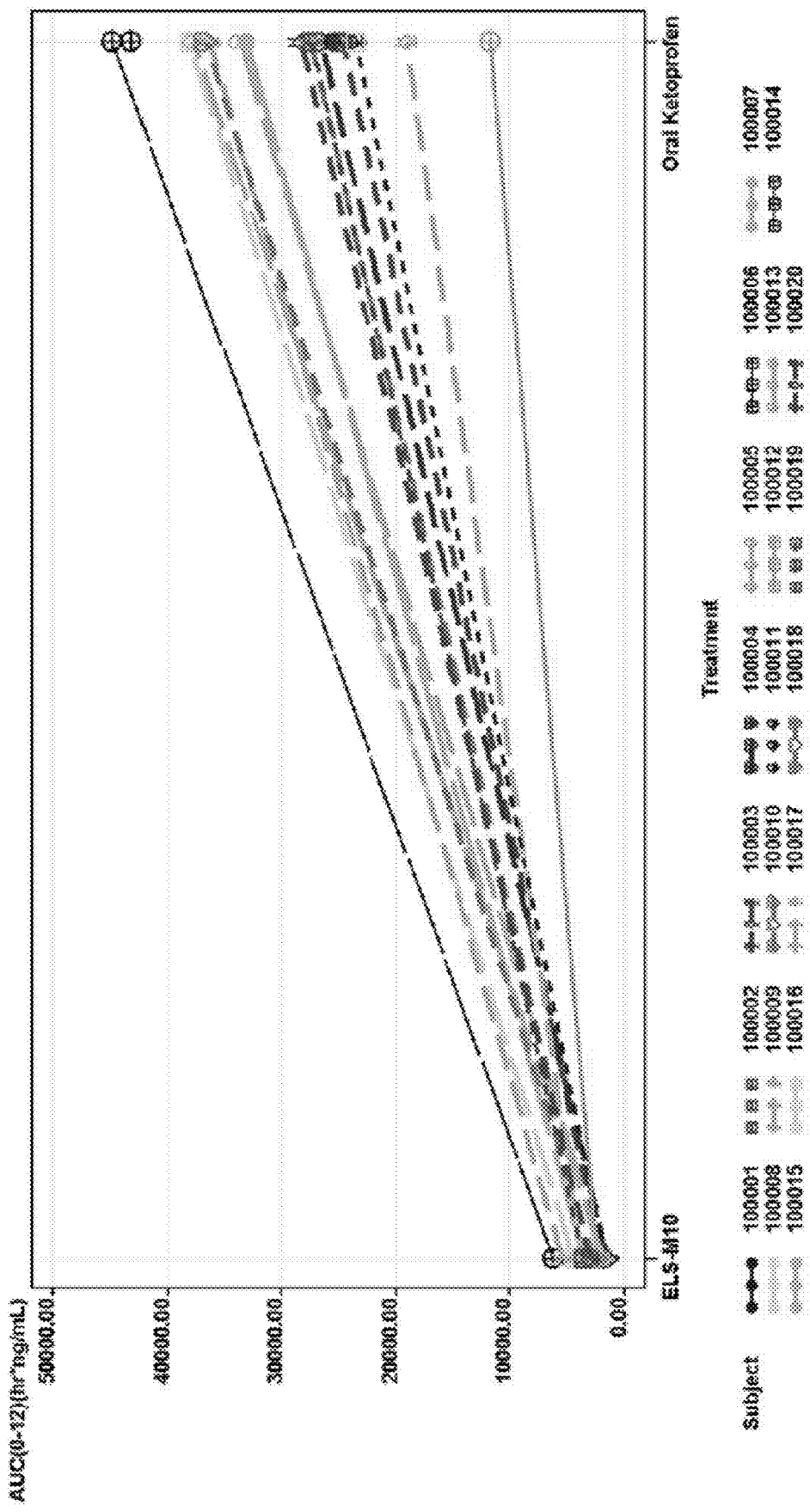
FIG. 4 is a plot of individual ketoprofen AUC(0-12) (area under plasma concentration vs. time curve from time 0 (i.e., time of dosing) to 12 hours post dose, calculated by linear trapezoidal method) across treatments.
Figure 5:
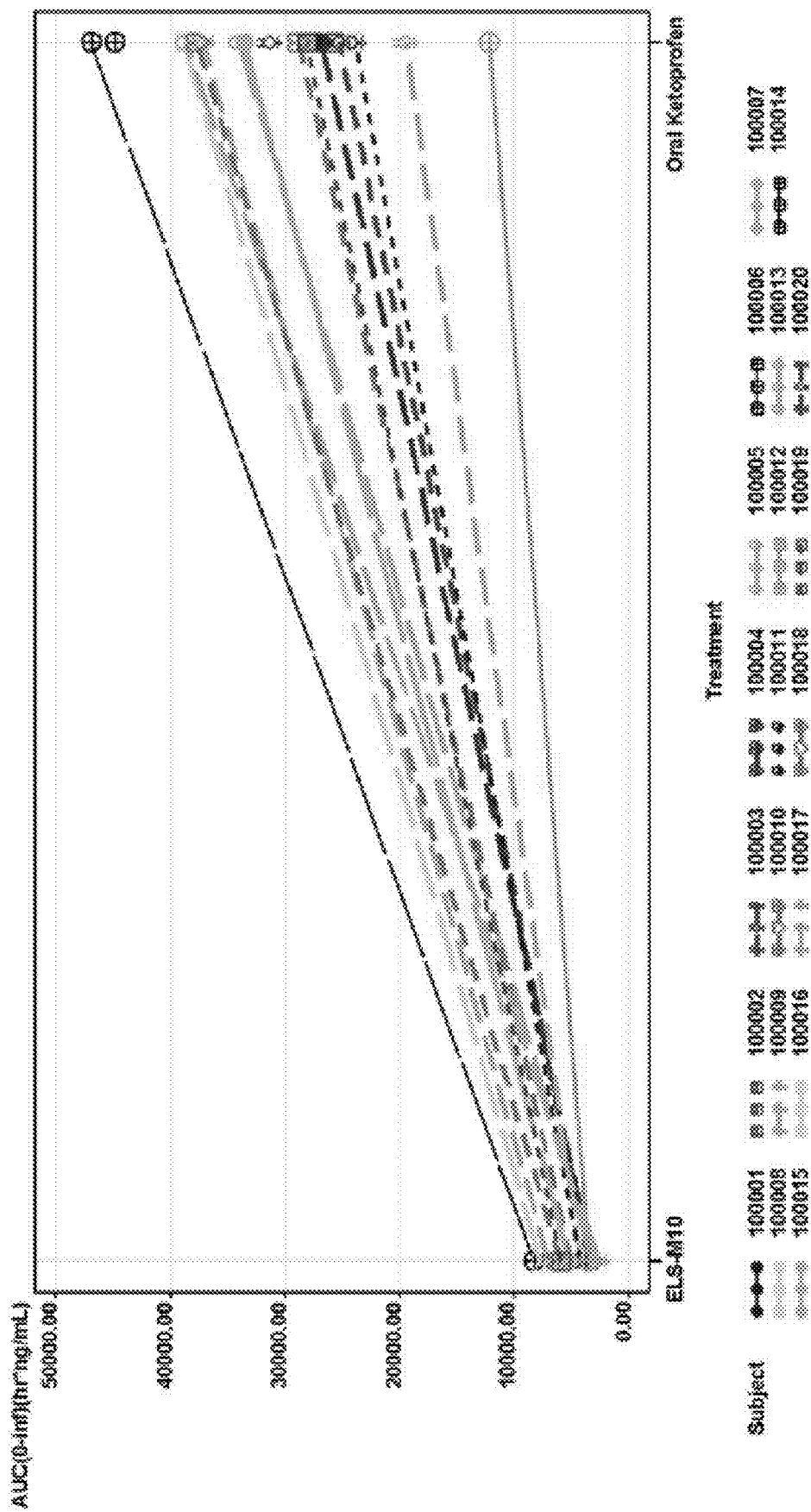
FIG. 5 is a plot of individual ketoprofen AUC(0-inf) (area under plasma concentration vs. time curve extrapolated to infinity, calculated as the sum of AUC(0t)Clast/$\lambda_z$ where Clast is the plasma concentration at Tlast) across treatments.
Figure 6:
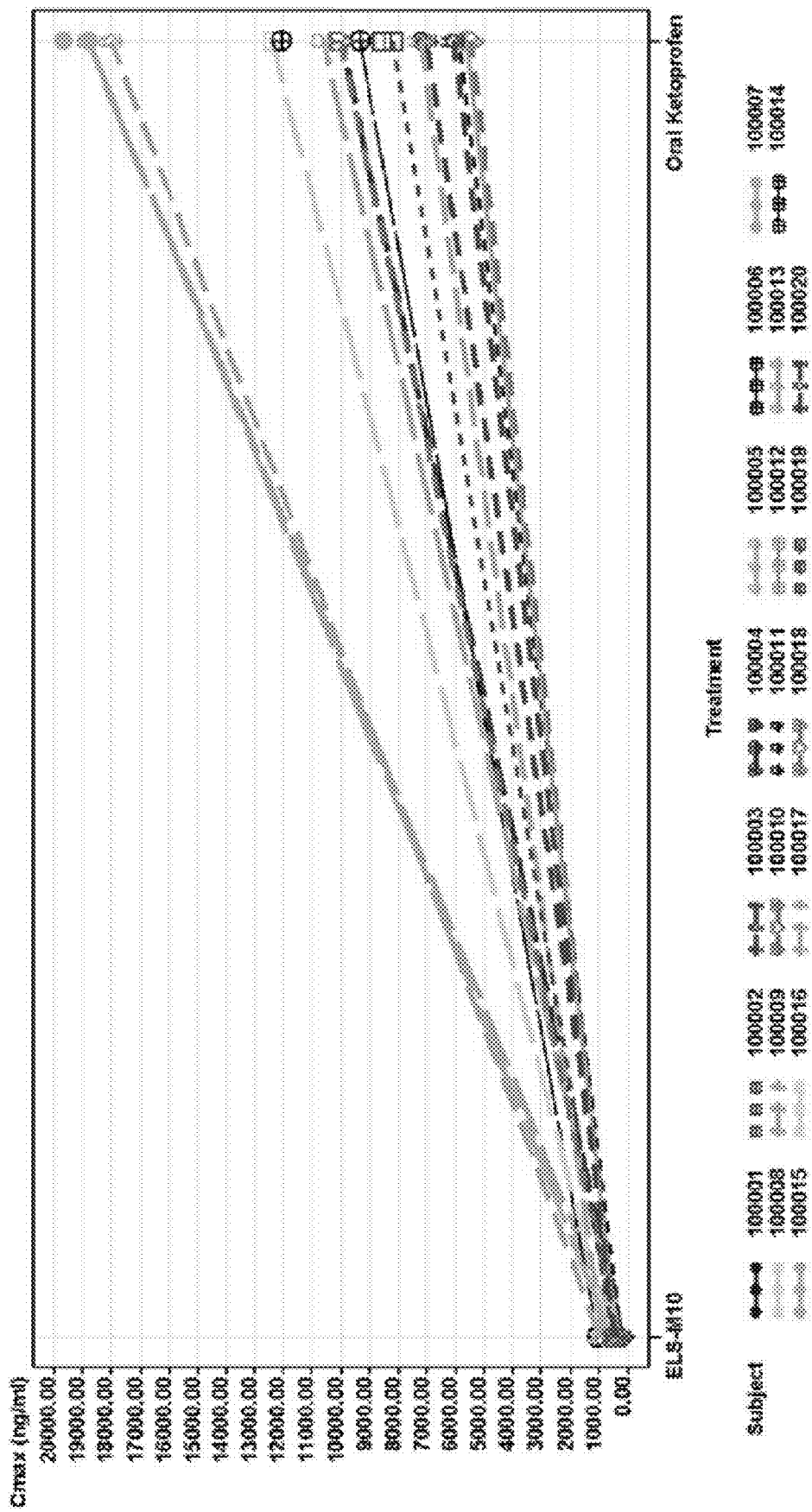
FIG. 6 is a plot of individual ketoprofen Cmax (first observed maximum plasma concentration in ng/mL) across treatments.
Figure 7:
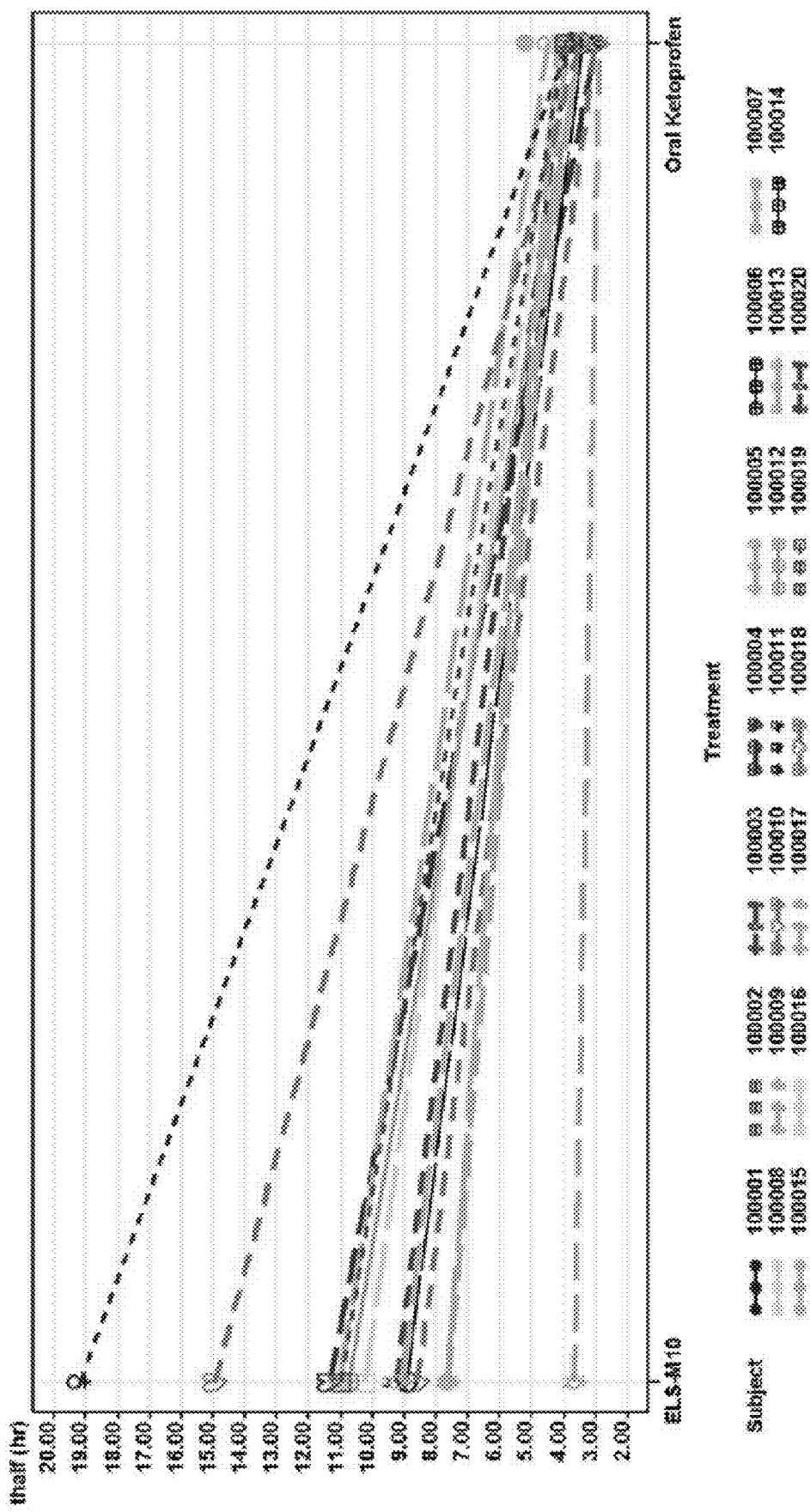
FIG. 7 is a plot of individual ketoprofen AUC($t_{half}$) (area under plasma concentration vs. time curve for apparent plasma elimination half-life calculated as 1 n2/$\lambda_z$) across treatments.
Figure 8:
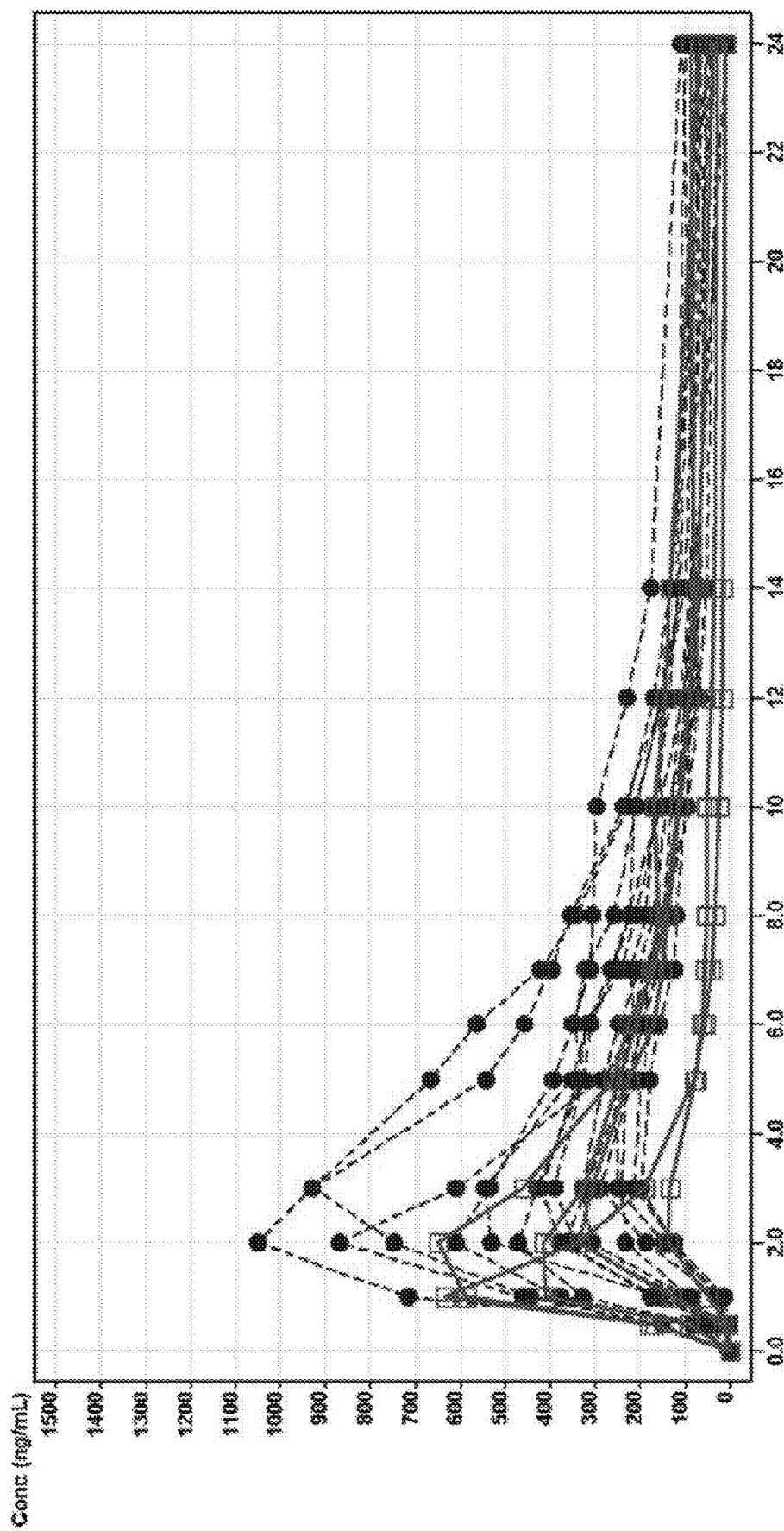
FIG. 8 is a plot of the plasma ketoprofen concentration vs. time curves for all subjects. Circles represent subjects with full exposure. Squares represent subjects with <hour exposure.

Exploratory analyses were performed on the five subjects who had early drug exposure withdrawal. The gel contact time for this subset of subjects ranged from 0.33 hours to 0.92 hours (0.33, 0.72, 0.75, 0.92). For the ELS-M10 treatment arm, FIG. 3 showed all patients overlaid with the treatment withdrawals color coded separate from the treatment completers. Table 15 shows summaries of the ELS-M10 ketoprofen pharmacokinetic parameters of these five patients along with the 15 fully exposed subjects.

TABLE 15

Summary of PK Parameter: Treatment Withdrawal Analysis Set

| Variable | Treatment | N | Geo. Mean | % CVb | Arith. Mean | Median | Min | Max |
|---|---|---|---|---|---|---|---|---|
| Half-life | Early Gel Removal | 5 | — | — | 12.36 | 11.96 | 9.5 | 15.4 |
| AUC(0-12) | Early Gel Removal | 5 | 1874.6 | 57 | 2076.1 | 2100.2 | 842 | 3191 |
| AUC(0-24) | Early Gel Removal | 5 | 2481.1 | 58 | 2752.4 | 3087.0 | 1213 | 3974 |
| AUC(0-inf) | Early Gel Removal | 5 | 3194.7 | 55 | 3519.5 | 4347.1 | 1775 | 4990 |
| $C_{max}$ | Early Gel Removal | 5 | 378.9 | 70 | 433.6 | 414.0 | 137 | 649 |
| $T_{max}$ | Early Gel Removal | 5 | — | — | 2.0 | 2.00 | 1.0 | 2.0 |

Tmax was seen an hour earlier for the five early treatment withdrawal subjects (median values of 2 hours versus 3 hours) versus the 15 ELS-M10 treatment completers. Although median maximum concentration levels for these five subjects was similar to the treatment completers (median(range) of 414(137,649) of ELS-M10 ketoprofen versus 391(197,1050) oral ketoprofen). Median total exposure as estimated by AUC(0-inf) was less in the early treatment withdrawal patients versus treatment completers by approximately 10% (median(rang) of 4347.1(1775,4990) of ELS-M10 ketoprofen versus 4687.4(2638,8201) oral ketoprofen).

ELS-M10 demonstrated promising pharmacokinetic properties. All subjects showed measurable levels of systemic ketoprofen concentrations where maximum ketoprofen concentrations were much lower for the topically applied ELS-M10 gel in treated subjects versus the maximum ketoprofen concentrations in subjects receiving oral ketoprofen. In addition, exposure parameters (AUC(0-inf), AUC(0-12) and AUC(0-24)), demonstrated lower systemic exposure for the ELS-M10 treated subjects versus the oral ketoprofen treated subjects even though the half-life for ELS-M10 ketoprofen was shown to be substantially longer than that of the oral ketoprofen.

Figure 9:
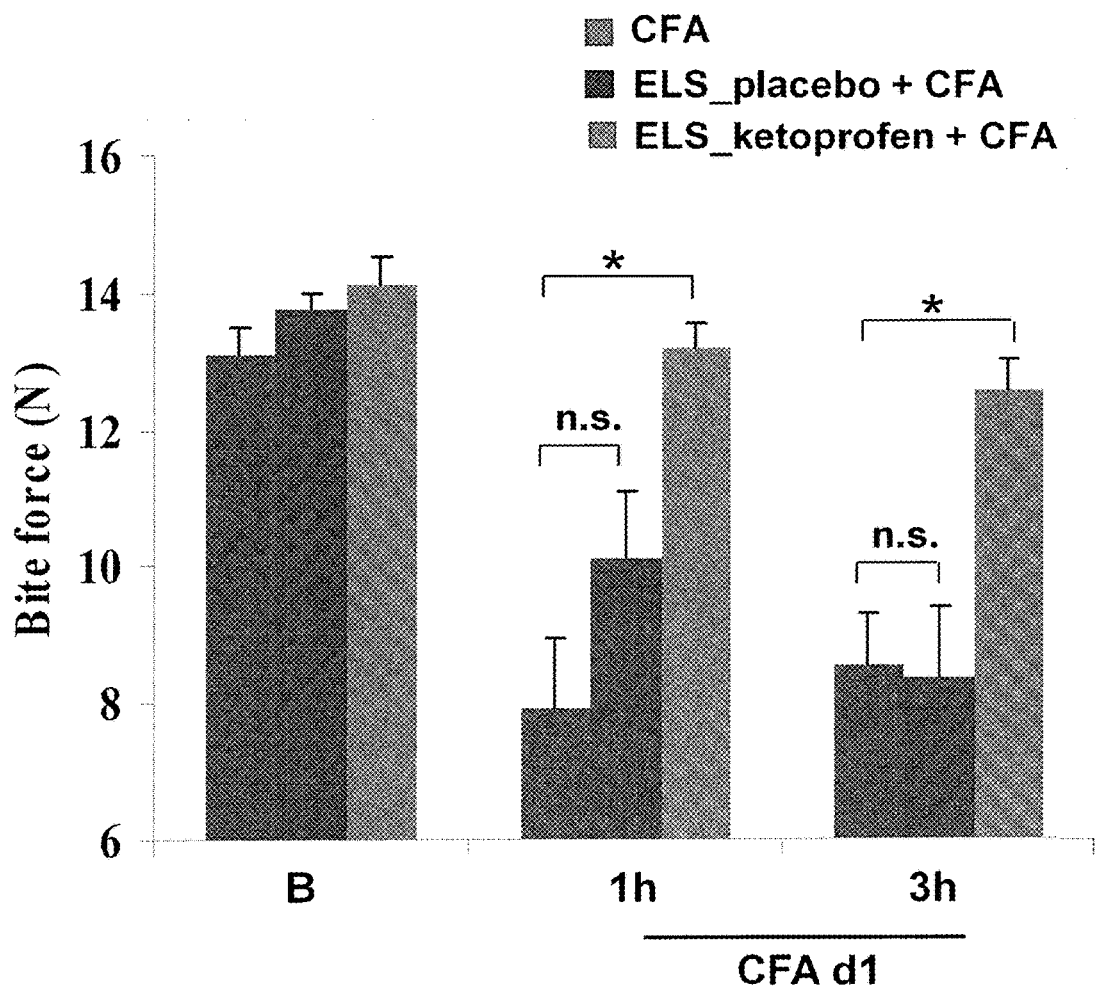
FIG. 9 is a graph showing topical application of ELS-M10 in an inflammation model of the temporomandibular joint. Bite force is measured at 24 hours post complete Freund's adjuvants (CFA) injection and 1 and 3 hours post treatment with ELS-M10.

Example 6: Effects of Topical Administration of ELS-Ketoprofen Formulation in Pre-Clinical Trigeminal Pain Models ELS-M10 and ELS-placebo were applied to the temporomandibular joints (TMJ) of mice that were sensitized by microinjections of complete Freund's adjuvants (CFA) into the temporomandibular joints bilaterally. This model and the subsequent metric of bite force were described by Chen et al. Pain. 2013 154(8):1295-304. Twenty four hours CFA injection was the peak of reduction of bite force. At 24 hours, ELS-M10 was applied topically to both TJM regions, by massaging a single dose into the TMJ area. Bite force was assessed 1 hour and 3 hours later. As seen in FIG. 9, bite force was restored to normal levels by topical treatment with ELS-M10 but not ELS-placebo. Thus, topical ELS-M10 is effective in this inflammatory model of TMJ pain. Further, without wishing to be bound by theory, it is believed that expression of cyclooxygenase (COX) in trigeminal ganglion sensory neurons is key to this effect, which relies on efficient transdermal targeting of trigeminal peripheral projections to the TMJ by ELS-M10 topical application.

Figure 10A:
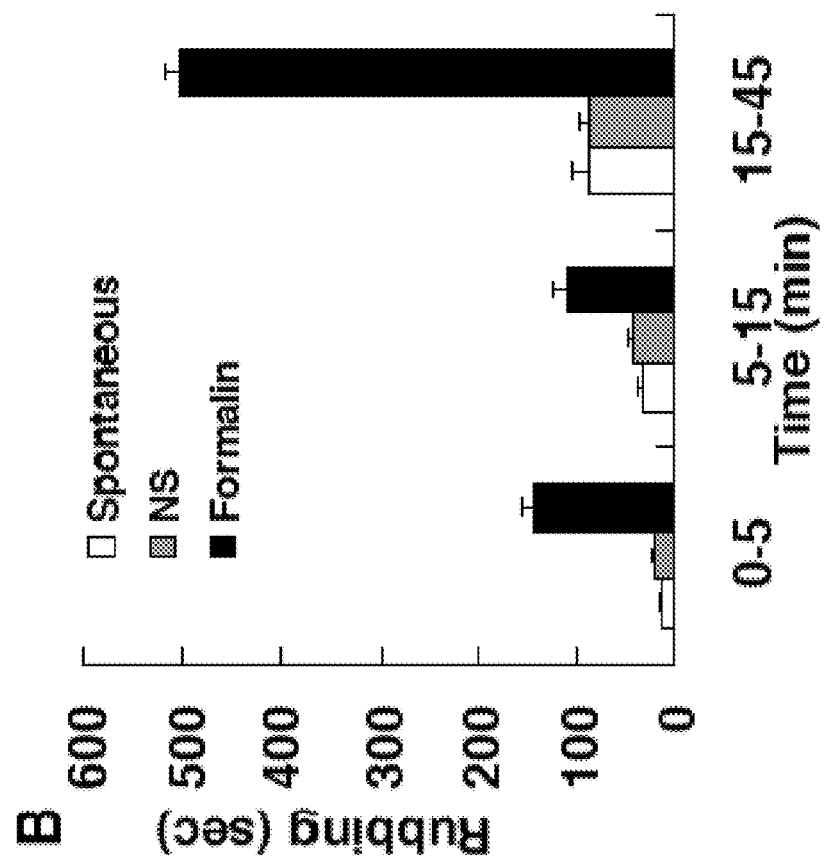
FIGS. 10A-10C are graphs showing the effects of topical application of ELS-M10 in a formalin irritant pain model to the mouse whisker pad.
Figure 10B:
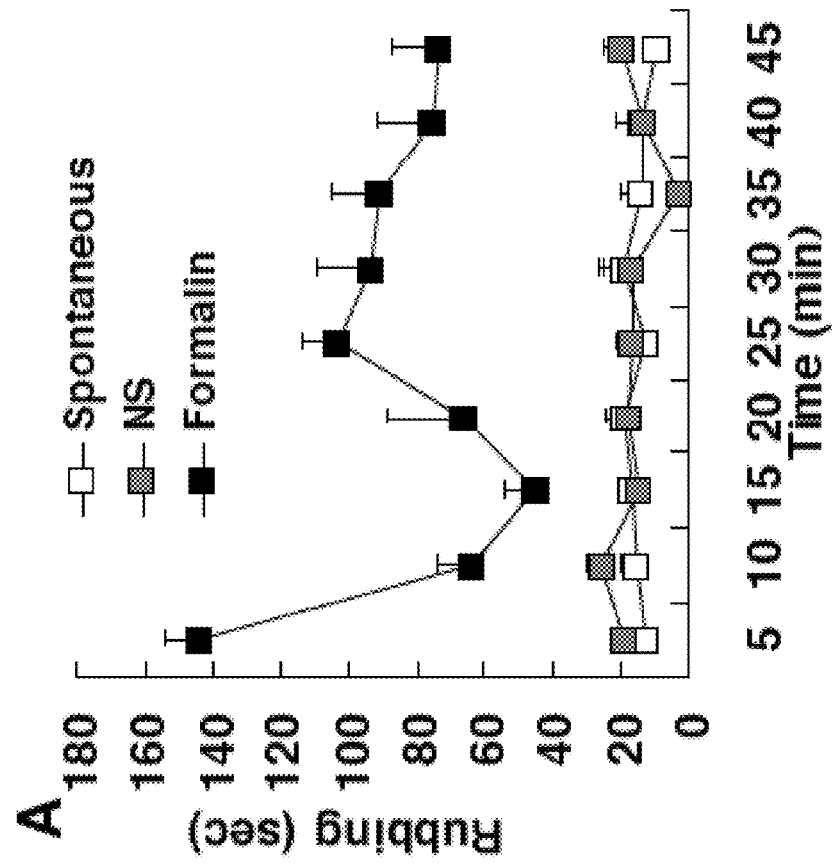
Figure 10C:
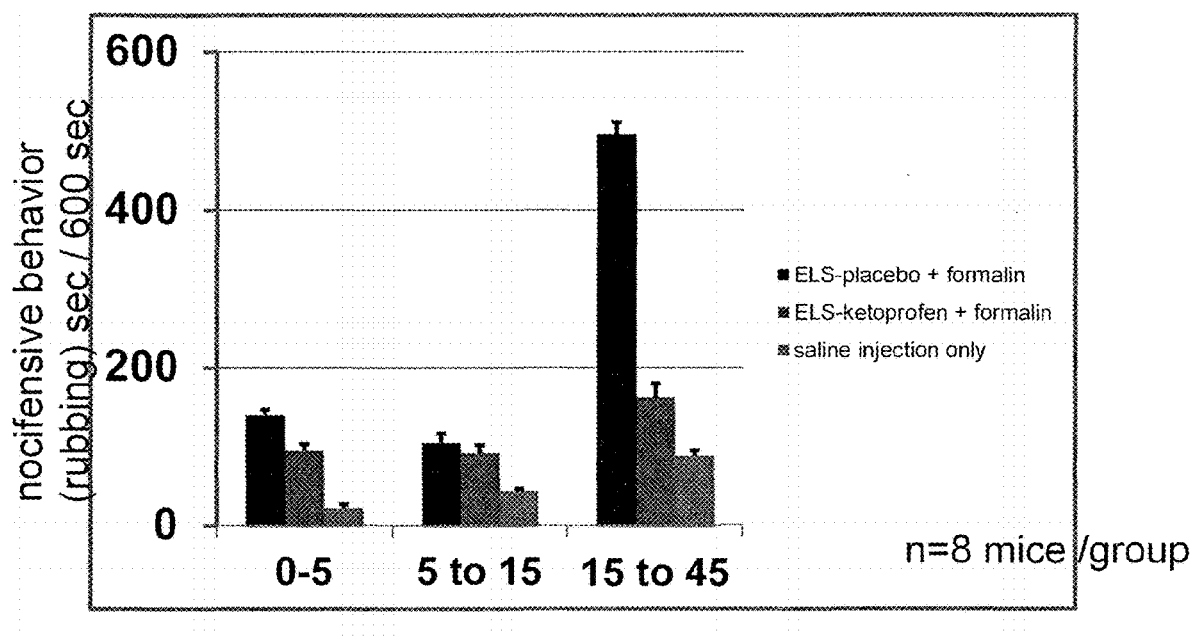

In another study, ELS-M10 topical application was assessed on the formalin irritant-pain model to the mouse whisker pad. In this model, the pain behavior is bi-phasic, as it is for the paw and pain behavior is increased with injection of equal volume/concentration of formalin into the paw, reflecting the higher sensitivity of the trigeminal system (FIGS. 10A-10B). As seen in FIG. 10C, topical application of ELS-M10 attenuates pain behavior in the acute, peripheral irritation phase and robustly attenuates pain behavior in the second, neuropathic phase. This finding indicates that ELS-M10 is effective against irritant induced trigeminal pain and acts sufficiently rapid to prevent the late phase of pain behavior. Moreover, the data are consistent with the effect of systemic ketoprofen on formalin pain behavior in the paw.

Figure 11:
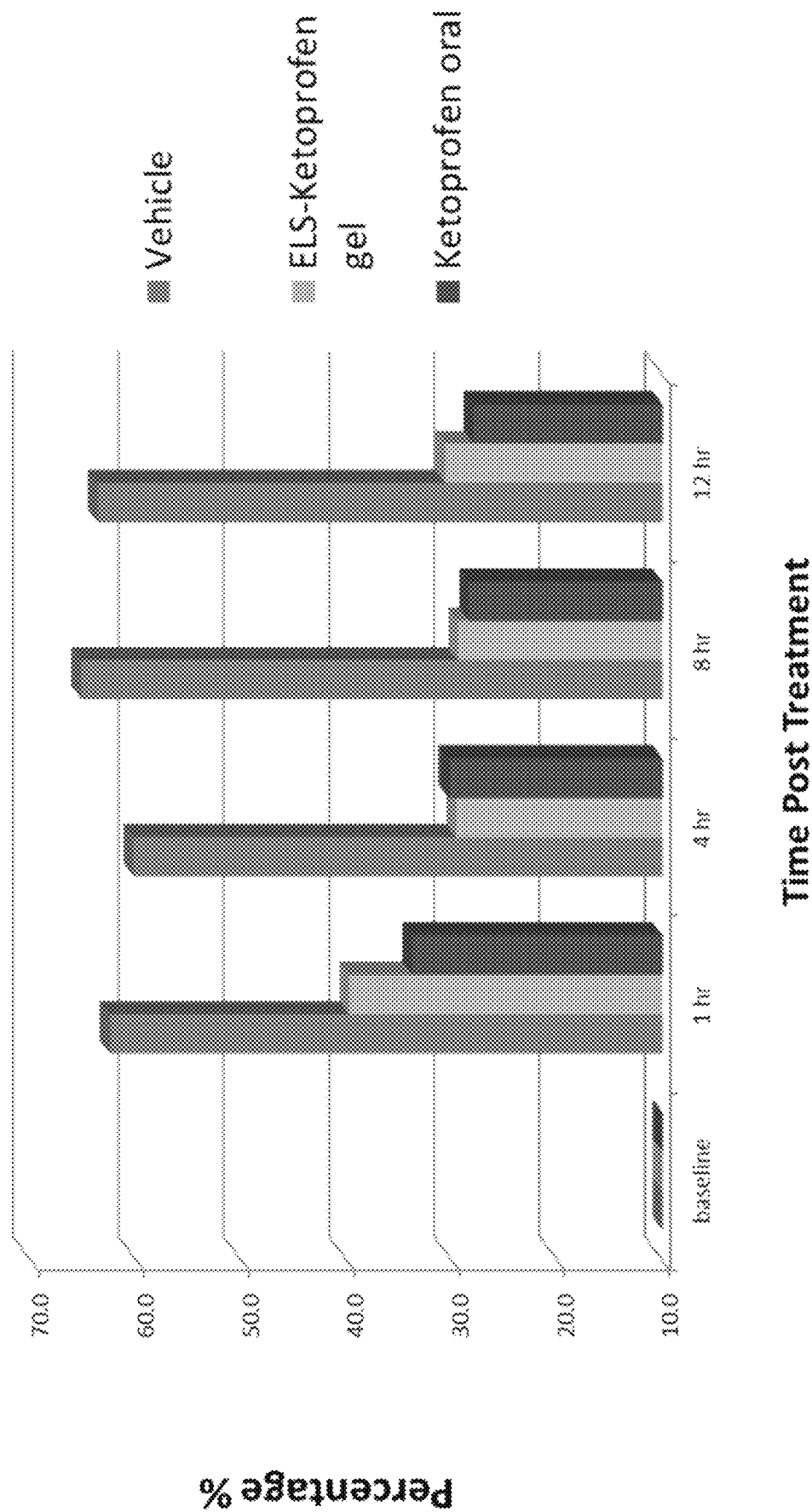
FIG. 11 is a graph showing weight bearing difference between paws (%) of rats upon topical application of ELS-M10 and oral administration of ketoprofen 1, 4, 8, and 12 hours post treatment.

In another study, the effects of topical application of ELS-M10 was compared to oral administration of ketoprofen on weight bearing in rats as a preclinical assessment of spontaneous pain. In this test, the animal is placed in an incapacitance meter where hind paws are on separate sensor plates. The test quantifies the spontaneous postural changes reflecting spontaneous pain by independently measuring the weight that the animal applies to each hind paw on two separate sensors. In the absence of hind paw injury, rats applied equal weight on both hind paws, indicating a postural equilibrium. After unilateral hind paw tissue injury, a change in the weight distribution on the sensor can be detected, with a lower weight applied by the injured paw, thus resulting in an increase in weight bearing difference between the paws. The weight bearing test is measured at baseline and day 1 (1, 4, 8, 12, and 24 hours post treatment) of treatment with topical ELS-M10 and oral ketoprofen. As seen in FIG. 11, the topical application of ELS-M10 decreased the percentage difference between the paws by half at 4 hours post treatment and comparable to the decrease seen in oral administration of ketoprofen. This study indicates that ELS-M10 is as effective as oral administration of ketoprofen in reducing spontaneous pain within a short time period (i.e., within 1 hour) after application.

Figure 12A:
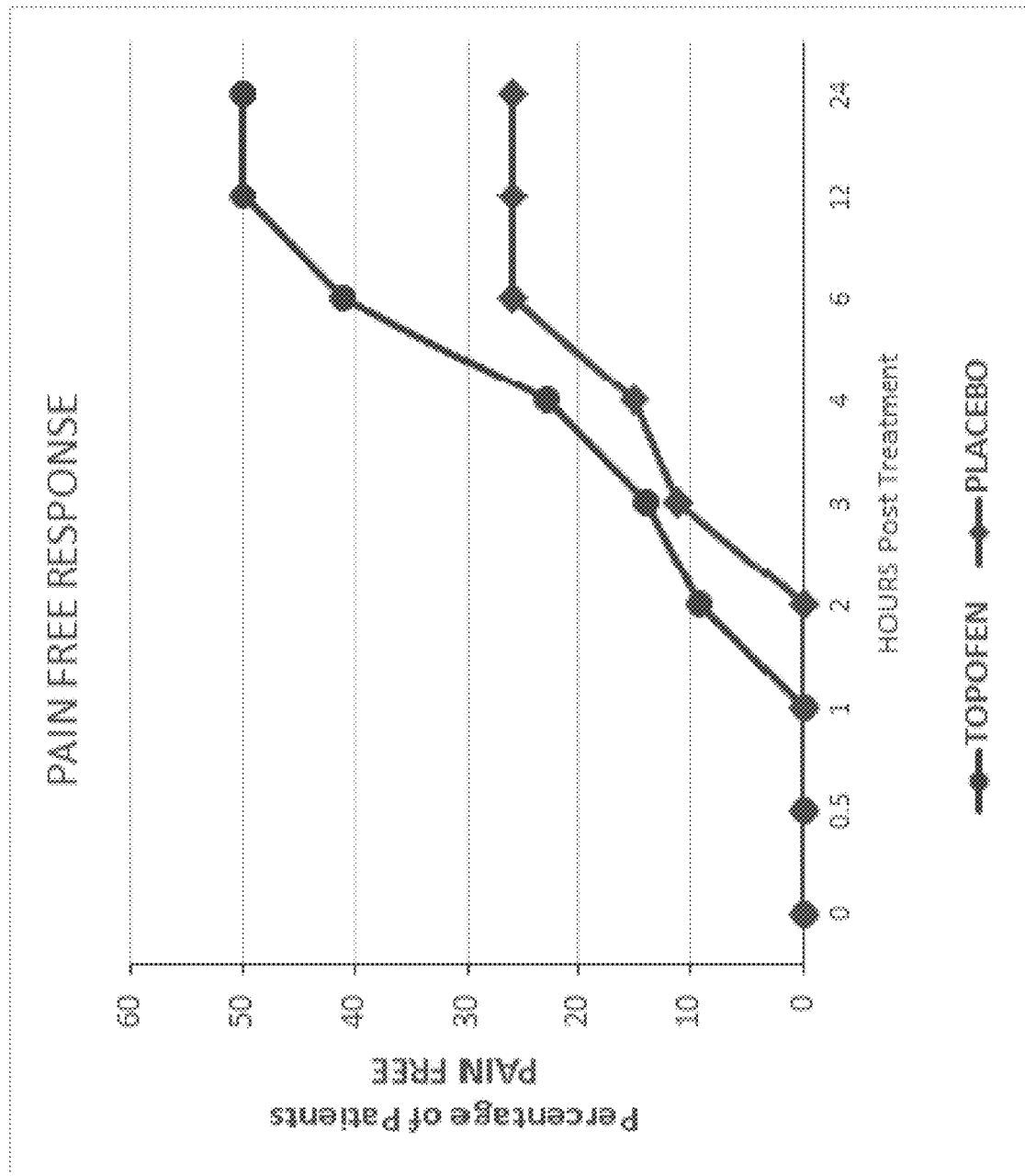
FIGS. 12A-12B are graphs showing the pain free response in human patients upon after initial topical application of ELS-M11.
Figure 12B:
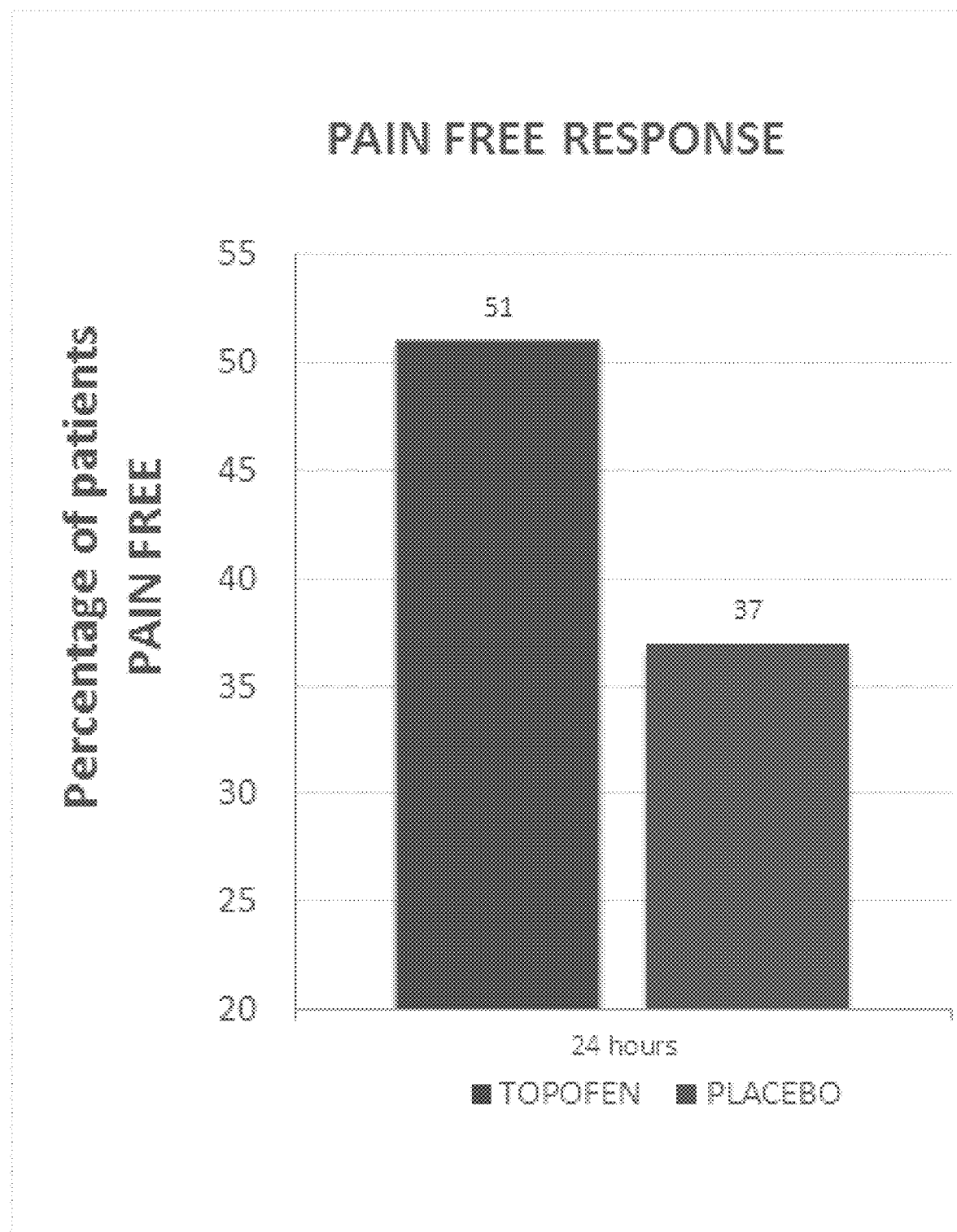
Figure 13:
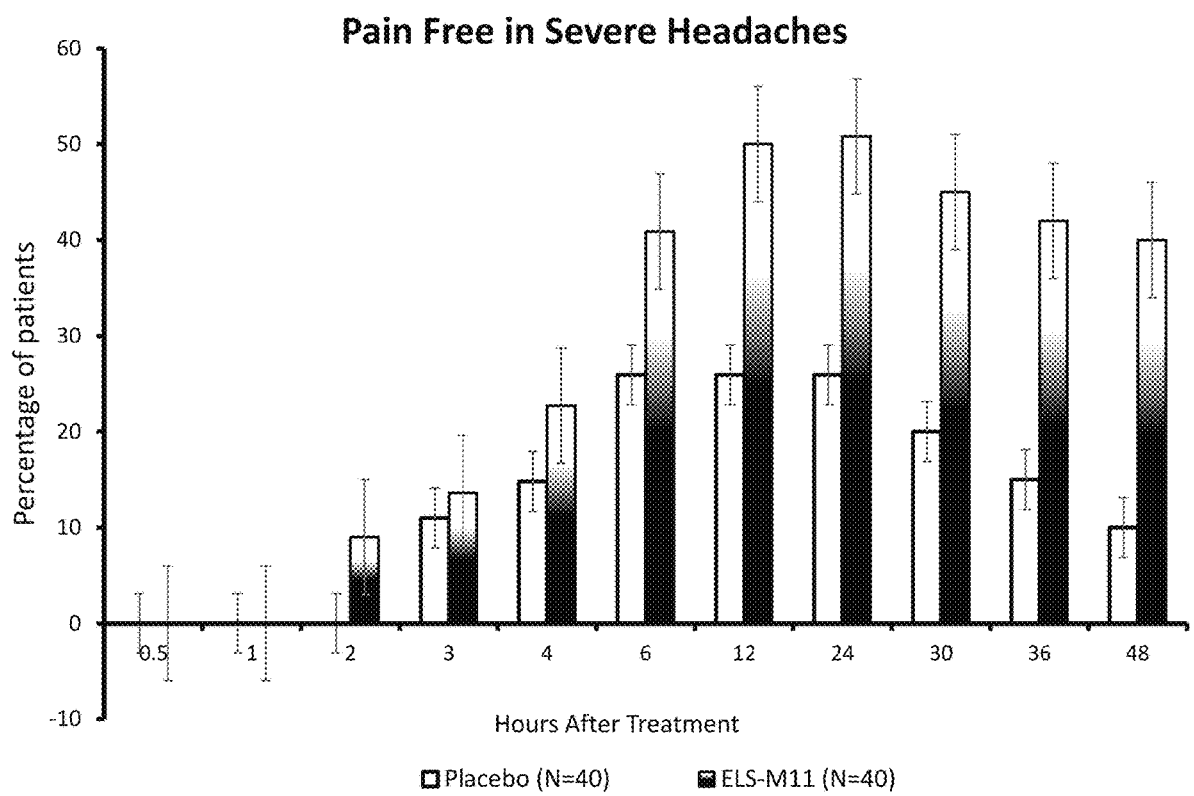
FIG. 13 is a graph showing the percentage of patients that were pain-free after a period of time (up to 48 hours) following bilateral administration of either placebo or ELS-M11 along the trigeminal nerve region.

Example 7: Topical Administration of ELS-Ketoprofen Formulation for Prophylactic Use Without wishing to be bound by theory, the pharmacokinetic properties of ELS-M10 and ELS-M11 make them desirable for use in prophylactic treatment of a migraine or symptom(s) of a migraine. As can be seen in FIGS. 12A and 12B, the pain free response in human patients after application of ELS-M11 is sustained for 24 hours after the initial application of the composition. These data suggest a possible use of the ELS-ketoprofen formulations as a prophylactic or preventative therapy. Consistent with these results, in a double-blind, placebo-controlled, randomized trial, patients with severe migraine treated their headache by application of 1 g of ELS-M11 (about 45 mg dose of ketoprofen) or placebo gel bilaterally (i.e., 0.5 g of composition to each side) along the trigeminal nerve region at time zero. The patients then followed their pain response for up to 48 hours. The results of their observations are provided in FIG. 13. As shown in FIG. 13, patients treated with ELS-M11 saw a prolonged protection against recurrent migraine headaches for as long as 48 hours attesting to the long duration of action of ketoprofen gel administered in accordance with the invention.

Prophylactic treatment is intended to reduce the frequency and intensity of migraine attacks. The prophylactic methods described herein do not necessarily result in complete freedom from symptoms associated with migraine attacks, but may provide for fewer symptoms or symptoms of reduced intensity. For many patients, it is the non-headache symptoms of migraine that are most disabling, and for which the patient is most desirous of relief. The prophylactic methods of the present invention are directed to the entire range of symptoms experienced by a patient during a migraine attack (e.g., throbbing pain on one side, aura, nausea, vomiting, sensitivity to bright lights, sensitivity to sounds, sensitivity to smells, blurry vision, neck pain, nasal stiffness, frequent urination, pallor, or sweating), and not merely at the prevention of headaches associated with a migraine attack.

The indications for preventative treatment of migraine have been published by the American Academy of Neurology. Prophylactic treatment is generally proposed for patients who suffer from two or more migraine attacks per month. Prophylactic treatment should also be considered for patients who experience less frequent migraine attacks that are more potent or even disabling. A third category of patients that may benefit from prophylactic treatment includes those who do not respond well to abortive treatments.

The compositions of the invention can also be useful for targeted prophylactic treatment of a migraine condition. The targeted prophylactic approach is relevant for persons with frequent, recurring migraine symptoms who anticipate critical activities during which it is very important to prevent or minimize their migraine-related symptoms. Furthermore, the targeted prophylactic approach may be especially relevant for persons who expect to experience a stimulus that is known to trigger migraine symptoms or is associated with an increased chance of experiencing migraine symptoms. For example, such stimuli include stress, change in routine, sleep, environmental stimuli (e.g., high altitude, weather changes, high humidity, loud noises), hormonal spikes (such as during regular or irregular menstrual cycles), glare (such as when starting at a computer screen, driving, skiing, flying, or boating on a clear day), food (e.g., a craving for sweet foods prior to experiencing migraines), lack of food, additives, alcohol, mild dehydration, drugs (e.g., taking drugs, e.g., cocaine and withdrawal from drugs), exercise, oral contraceptives, teeth grinding, or physical conditions (e.g., head injury, muscle tension, coughing). The method for targeted prophylactic treatment includes determining a time window or selected time period in which a patient desires to be free from migraine or a symptom of migraine; and administering to the patient, at a time prior to the determined time window, a therapeutically effective amount of a therapeutic agent (e.g., any described herein, e.g., an NSAID, e.g., ELS-M10), either alone or in combination with a second agent (e.g., a corticosteroid, acetaminophen, an opioid, a muscle relaxant, an anti-anxiety drug, an anti-depressant, an anti-convulsant drug, an antipsychotic, an antiepileptic drug, and a selective serotonin reuptake inhibitor (SSRI)), to prevent or reduce migraine symptoms during the time window. The therapeutic agent can further be administered (e.g., any described herein, e.g., an NSAID, e.g., ELS-M10) alone or in combination with non pharmacological treatments (e.g., relaxation techniques, bio-feedback, cognitive behavioural therapy, and/or acupuncture) for the prophylactic treatment of a migraine or symptom associated with a migraine.

The time window would include the period of time over which the patient anticipates participating in the critical activities during which the patient desires to be as free from migraine symptoms as is possible, or the period over which a patient expects to experience a migraine-triggering stimulus. The time window or selected time period could also include a period (lasting hours or several days) after a known or probable migraine-inducing stimulus, such as the consumption of red wine, disruption of sleep, or a skipped meal.

For example, a patient with an established history of migraine brought on by occasional consumption of red wine (as a beverage or in a sauce or dressing) can apply ELS-M10 on the same day as such consumption before migraine attack symptoms are evident. The patient will be free of, or experience substantially reduced, migraine symptoms for a time period during which symptoms would normally be experienced or expected in the absence of application of ELS-M10.

In another example, a patient with an established history of recurrent migraine can be treated with once a day application of ELS-M10. The patient will be free of migraine symptoms during the first week of use and notice a reduced intensity of the symptoms of subsequent migraine attacks as well as a reduced frequency of migraine attacks during the treatment period of three to four weeks.

In another example, a patient with an established history of migraine brought on by glare associated with an ophthalmic operating room microscope can apply ELS-M10 the night before or the week before (depending on the severity of the migraine when it occurs) the scheduled ophthalmic operation. The patient will be free of migraine symptoms before, during and after the scheduled operation after targeted prophylactic treatment with ELS-M10 alone or in combination with a second agent. The patient may also experience migraine symptoms at a greatly reduced intensity as compared to a full-fledged migraine, so that he was able to function effectively during the scheduled operations.

In another example, a patient with a well-established history of recurrent migraine attacks learns to recognize his/her prodromal symptoms of altered mood, irritability, fatigue, and craving for sweets which typically occur 3 to 24 hours prior to the fully developed phase of his migraine.

He/she learns over time that these prodromal symptoms eventually lead to a migraine attack in most cases. His/her migraine attacks typically include unusual sensitivity to light and sound, difficulty concentrating, headache, and less commonly, nausea. As soon as he/she recognizes the prodromal symptoms, he/she applies a one-time dose of ELS-M10. He/she notes that he/she is either free of, or has greatly reduced, migraine attack symptoms subsequent to applying ELS-M10. Continued daily dosing extends that period of benefit for several days (or longer) subsequent to the initial symptoms.

In another example, a middle-aged female patient with a well-established history of recurrent migraine attacks heralded by an aura of dysphasia (i.e., difficulty in finding words) applies ELS-M10 at the onset of the dysphasic symptoms. She notes a reduction in the intensity and length of the migraine attack symptoms which usually, but not always, follow the aura. Because she has lately suffered more than four migraine attacks per month, on the advice of her physician she continues daily dosing of ELS-M10 over time. She then notes a substantial decrease in the frequency and intensity of the migraine attacks while continuing to apply ELS-M10.

For some of these patients, it is possible that early or premonitory migraine symptoms (e.g., keeping a migraine diary or a trigger diary) will be evident at the time of administration of the agent or agents to be used for treatment, but the administration will still take place prior to the critical activities or expected stimulus. In this case, the treatment may be termed "acutely targeted" if the goal is to eliminate or substantially reduce the migraine symptoms during the particular time or activity for the patient. Often, the patient will learn to recognize early or premonitory migraine symptoms, or will be aware of a pattern or frequency of migraine attacks, and will be able to self-administer the treatment at an appropriate time.

In other cases, there will be no early or premonitory symptoms of migraine when this agent or agents are administered for targeted prophylaxis. This dosing strategy is very useful for those persons with frequent, recurring stimuli or high-demand activities that are associated with frequent migraine symptoms. Again, the patient may be able to self-administer at an appropriate time, when the patient anticipates participating in a critical activity or the patient expects to experience a migraine-triggering stimulus.

OTHER EMBODIMENTS

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, pharmacology, or related fields are intended to be within the scope of the invention. All publications, patent applications, and patents mentioned in this specification are herein incorporated by reference.

What is claimed is:

1. A method of treating pain or inflammation associated with a temporomandibular disorder (TMD) in a subject in need thereof, said method comprising topically administering to said subject a sustained release composition comprising from about 0.5% (w/w) to about 5% (w/w) of a therapeutic agent and a dermatologically acceptable excipient, wherein said composition is in an amount effective to treat said temporomandibular disorder (TMD) in said subject; wherein administration of said composition to said subject results in a peak plasma concentration of said therapeutic agent at three hours that is at most about 450 ng/mL; wherein said therapeutic agent is ketoprofen; and wherein said composition comprises from about 20 mg to about 200 mg of ketoprofen in unit dosage form.

2. The method of claim 1, wherein said peak plasma concentration of said therapeutic agent when administered topically is lower than the peak plasma concentration of said therapeutic agent when administered orally.

3. The method of claim 1, wherein administration of said composition to said subject provides for gradual release of said therapeutic agent over 2-24 hours.

4. The method of claim 3, wherein administration of said composition results in a plasma concentration of said therapeutic agent that is maintained between about 50 ng/mL and about 150 ng/mL for up to 24 hours.

5. The method of claim 1, wherein the half-life of said therapeutic agent is from about 7 to about 13 hours.

6. The method of claim 1, further comprising monitoring whether the subject experiences amelioration of the pain or inflammation associated with TMD.

7. The method of claim 1, wherein said composition comprises a total maximum dosage of about 135 mg of ketoprofen.

8. The method of claim 1, wherein said composition is formulated as a gel, cream, lotion, ointment, foam, powder, solution, spray, emulsion, or suspension for topical administration.

9. The method of claim 8, wherein said composition if formulated as a gel for topical administration.

10. The method of claim 1, wherein said composition is administered one or more times a day.

11. The method of claim 1, wherein said composition is administered for one day or at least two to twenty days.

12. The method of claim 1, wherein said composition is administered for more than twenty days.

13. The method of claim 1, wherein said composition is administered with a second agent.

14. The method of claim 13, wherein said second agent is selected from the group consisting of: a corticosteroid, acetaminophen, an opioid, a muscle relaxant, an anti-anxiety drug, an anti-depressant, an anti-convulsant drug, an antipsychotic, an antiepileptic drug, and a selective serotonin reuptake inhibitor (SSRI).

* * * * *